United States Patent
Duprat et al.

(10) Patent No.: US 9,084,778 B2
(45) Date of Patent: Jul. 21, 2015

(54) TOPICAL COMPOSITIONS CONTAINING A RETINOID OF THE OIL-IN-WATER EMULSION TYPE

(71) Applicant: GALDERMA RESEARCH & DEVELOPMENT, Biot (FR)

(72) Inventors: Agnes Duprat, Mougins (FR); Claire Mallard, Mougins (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 13/906,336

(22) Filed: May 30, 2013

(65) Prior Publication Data

US 2013/0331428 A1  Dec. 12, 2013

Related U.S. Application Data

(60) Provisional application No. 61/654,729, filed on Jun. 1, 2012.

(51) Int. Cl.
*A61K 31/402* (2006.01)
*A61K 9/10* (2006.01)
*A61K 9/107* (2006.01)

(52) U.S. Cl.
CPC ............... *A61K 31/402* (2013.01); *A61K 9/107* (2013.01)

(58) Field of Classification Search
CPC .... A61K 31/402; A61K 31/107; A61K 9/107
USPC .......................................... 514/424, 458, 474
See application file for complete search history.

(56) References Cited

U.S. PATENT DOCUMENTS 5,851,538 A    12/1998   Froix et al.

FOREIGN PATENT DOCUMENTS

| EP | 0 826 366 B1 | 10/2003 |
|----|---|---|
| EP | 0 989 846 B1 | 11/2004 |
| EP | 1 831 149 B1 | 1/2012 |

*Primary Examiner* — Raymond Henley, III
(74) *Attorney, Agent, or Firm* — Dentons US LLP

(57) ABSTRACT

A composition in the form of an oil in water emulsion, preferably without emulsifier, is described. The composition can include, in a physiologically acceptable environment, at least one new retinoid. Also described, is the method of preparing the composition and its use in cosmetics and dermatology.

73 Claims, 3 Drawing Sheets

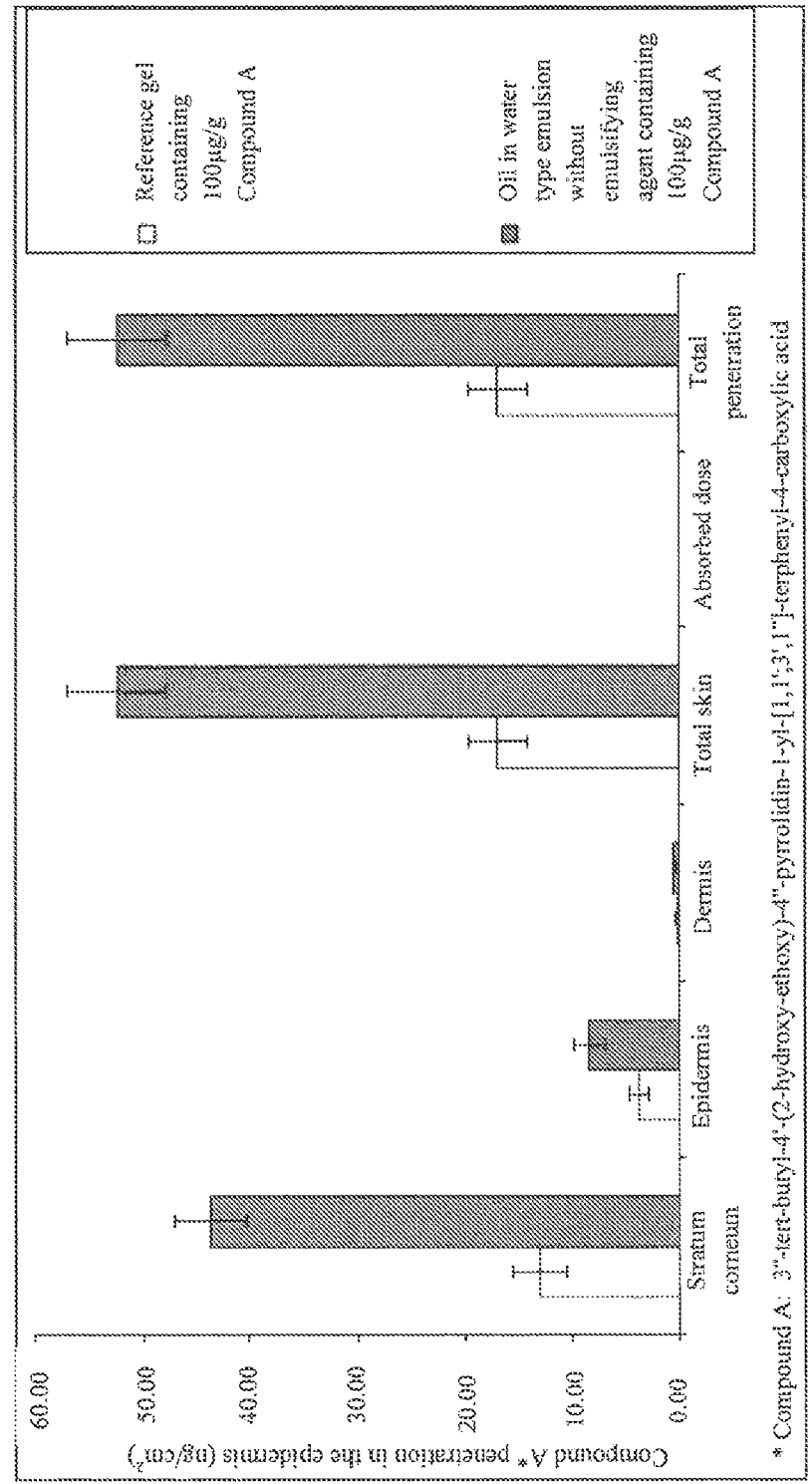

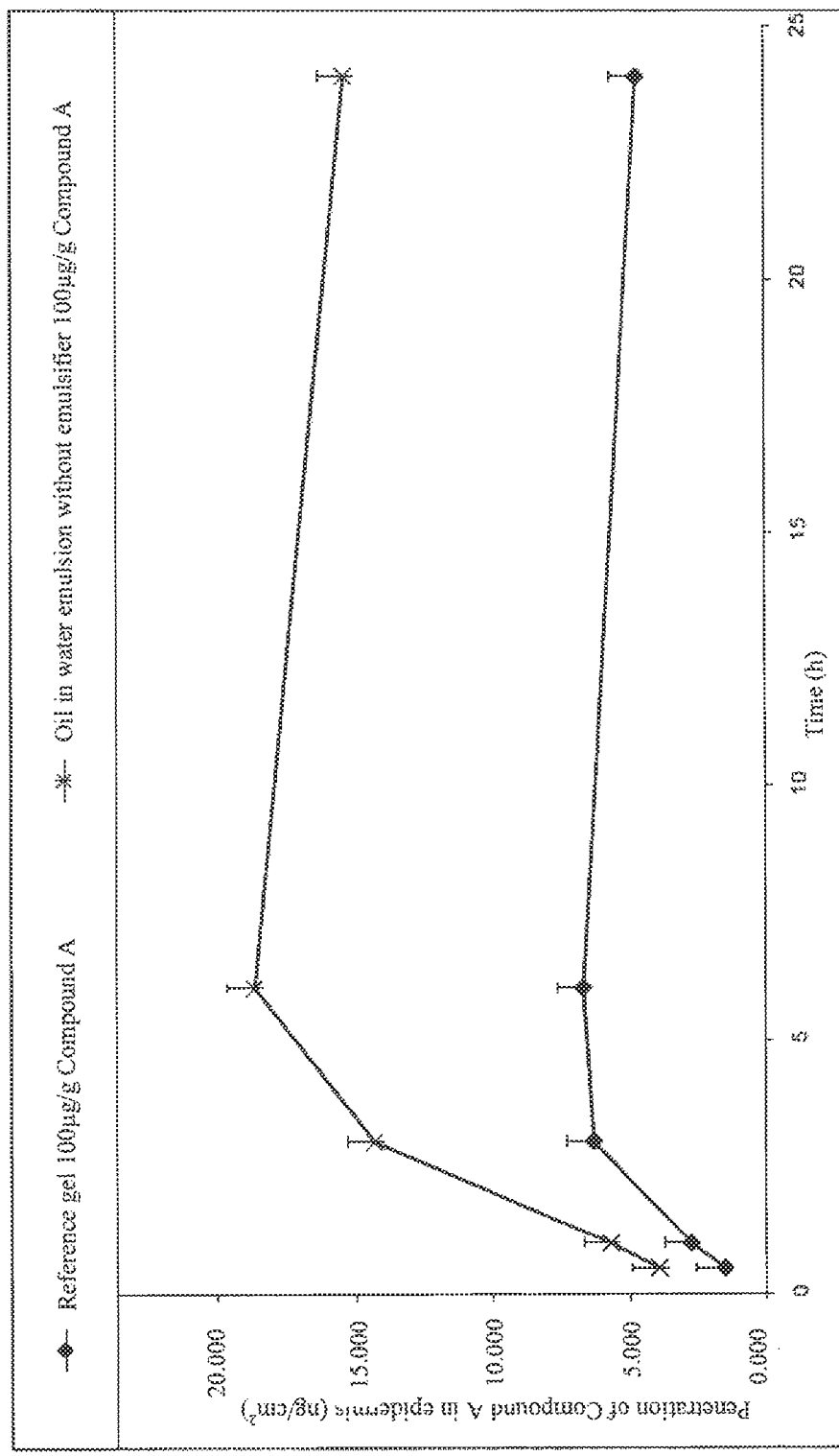

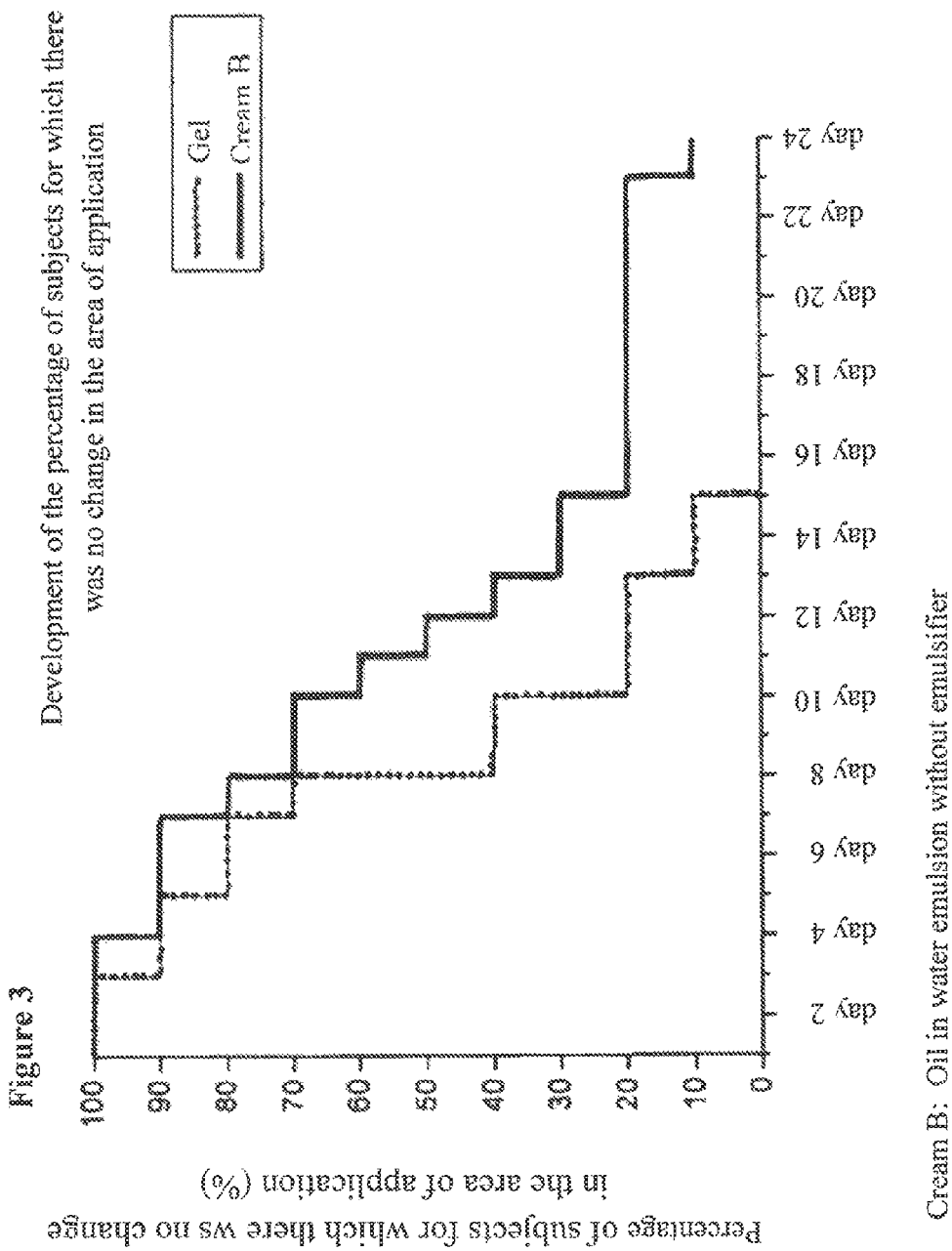

TOPICAL COMPOSITIONS CONTAINING A RETINOID OF THE OIL-IN-WATER EMULSION TYPE

CROSS-REFERENCE TO EARLIER APPLICATION

This application is a non provisional of U.S. Application No. 61/654,729, filed Jun. 1, 2012, which is hereby expressly incorporated by reference in its entirety.

The invention relates to a composition in the form of emulsion comprising, in a physiologically environment, at least one new retinoid with the general formula (I)

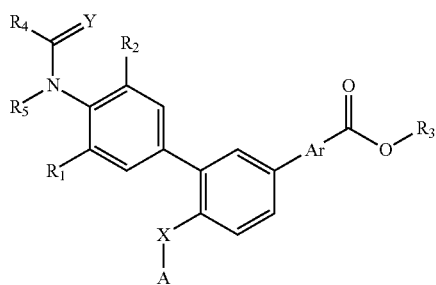

where:
- $R_1$ is a hydrogen atom, an alkyl radical of 1 to 4 carbon atoms or a —$CF_3$ radical;
- $R_2$ is a hydrogen atom, an alkyl or alkoxy radical of 1 to 4 carbon atoms or a chlorine atom;
- $R_3$ is a hydrogen atom, an alkyl or alkoxy radical of 1 to 10 linear or branched carbon atoms, possibly substituted by a methoxy group;
- $R_4$ is a hydrogen atom or an alkyl radical of 1 to 3 carbon atoms;
- $R_5$ is a hydrogen atom or an alkyl radical of 1 to 3 carbon atoms;
- or $R_4$ and $R_5$ together form, with the bond —N—C(=Y)—, a ring of the type pyrrolidine, pyrrolidinone, piperidine or piperidinone;
- Y denotes two hydrogen atoms or one heteroatom such as oxygen or sulphur;
- Ar denotes a cyclo 1,4-phenyl, 2,5-pyridyl, 5,2-pyridyl or 2,5-thiophenyl;
- X denotes an oxygen atom, possibly substituted by an alkyl or alkylamine chain or a single C—C bond;
- A denotes a hydrogen atom or the following formula:

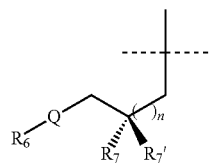

where
- Q is an oxygen atom or the bond —NH—;
- $R_6$ denotes a hydrogen atom, an alkyl radical of 1 to 6 carbon atoms, a cycloalkyl radical of 3 to 6 carbon atoms, a —$C(O)CH_2$ or —$C(O)CH_2CH_3$ radical;
- $R_7$ and $R_7'$ denote, independently of each other, a hydrogen atom or a hydroxyl group, on condition that $R_7$ and $R_7'$ are not simultaneously a hydroxyl group;
- n is equal to 0, 1, 2, 3, 4 or 5;

These compounds, described in patent EP1831149, are potent retinoids modulating the nuclear receptor/receptors of retinoic acid (RAR), more specifically of the gamma subtype of this receptor (RARγ).

The receptors RARs activate the transcription by binding with elements of DNA sequences, called the RAR Element (RARE) response elements, in the form of a heterodimer with the X receptors of the retinoids (called RXRs).

Three subtypes of human RARs have been identified and described: RARα, RARβ and RARγ.

Since the gamma RAR receptors are located in the epidermis it is important for the compounds described in the general formula (I) to be released in this part of the skin to provide clinical efficacy.

The topical application of retinoids may result in irrigation of the skin, dryness and erythema. Numerous articles describe this irritating effect, such as the articles by Stucker & al. Skin Res Technol. 2002 May; 8(2):133-40 or by Thielitz & al. Am J Clin Dermatol. 2008; 9(6):369-81.

To obtain topical preparations for pharmaceutical use containing retinoids, numerous techniques are used, in particular emulsions such as those referred to in the patent EP-826366, which describes emulsions which may contain retinoids, or even patent EP-989846, which describes emulsions containing retinoids and at least one emulsifier.

Emulsifiers are molecules that belong to the chemical family of amphiphilic molecules, which are often irritating. Compositions without emulsifiers are in fact less irritating that those containing them.

The fact that emulsifiers are not used in the compositions containing retinoids would therefore enable eliminating cutaneous irritation due to the presence of this class of molecule.

The prior art describes H/E emulsions with or without emulsifier. We may cite, in particular, U.S. Pat. No. 5,851,538, which describes formulations with or without emulsifier with porous microspheres containing a practically continuous network of pores open to the outside and comprising retinoids.

Nevertheless, although the compounds described by the general formula (I) exhibit interesting chemical and physical stability properties for preparations for pharmaceutical uses, they degrade chemically in a number of their solvents.

There is therefore a need for stable, well tolerated pharmaceutical compositions containing compounds described by general formula (I).

A first object according to the invention relates to a pharmaceutical composition comprising a compound with the general formula (I)

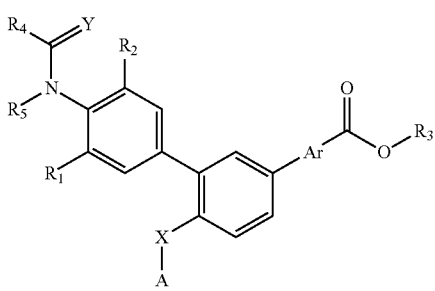

where:
- $R_1$ is a hydrogen atom, an alkyl radical of 1 to 4 carbon atoms or a —$CF_3$ radical;

$R_2$ is a hydrogen atom, an alkyl or alkoxy radical of 1 to 4 carbon atoms or a chlorine atom;

$R_3$ is a hydrogen atom, an alkyl or alkoxy radical of 1 to 10 linear or branched carbon atoms, possibly substituted by a methoxy group;

$R_4$ is a hydrogen atom or an alkyl radical of 1 to 3 carbon atoms;

$R_5$ is a hydrogen atom or an alkyl radical of 1 to 3 carbon atoms;

or $R_4$ and $R_5$ together form, with the bond —N—C(=Y)—, a ring of the type pyrrolidine, pyrrolidinone, piperidine or piperidinone;

Y denotes two hydrogen atoms or one heteroatom such as oxygen or sulphur;

Ar denotes a 1,4-phenyl, 2,5-pyridyl, 5,2-pyridyl or 2,5-thiophenyl ring;

X denotes an oxygen atom, possibly substituted by an alkyl or alkyamine chain or a single C—C bond;

A denotes a hydrogen atom or the following formula:

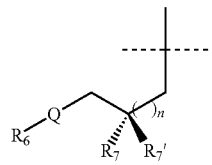

where:

Q is an oxygen atom or the bond —NH—;

$R_6$ denotes a hydrogen atom, an alkyl radical of 1 to 6 carbon atoms, a cycloalkyl radical of 3 to 6 carbon atoms, a —C(O)CH$_2$ or —C(O)CH$_2$CH$_3$ radical;

$R_7$ and $R_7'$ denote, independently of each other, a hydrogen atom or a hydroxyl group, on condition that $R_7$ and $R_7'$ are not simultaneously a hydroxyl group;

n is equal to 0, 1, 2, 3, 4 or 5;

at least one gelling agent of the aqueous phase, at least one principal solvent of the compound (I) and at least one co-solvent oil of the compound (I).

A second object according to the invention relates to a pharmaceutical composition such as described above for its use as a medicinal product.

A third object according to the invention relates to a pharmaceutical composition as described above for its use in the treatment of pathologies such as:

1) dermatological complaints associated with a keratinisation disorder relating to cellular differentiation and proliferation, particularly for treating common, comedonic, polymorphic acnes, rosaceas, nodulocystic acnes, conglobata, senile acnes and secondary acnes such as solar, medicamentous or professional acne;

2) keratinisation disorders, in particular ichtyoses, ichtyosiform conditions, lamellar ichtyosis, Darrier's disease, palmoplantar keratodermias, leukoplasias, pityriasis rubra pilaris and leukoplasiform conditions, cutaneous or mucous (oral) lichen;

3) dermatological disorders with an inflammatory immune-allergic component, with or without cellular proliferation disorder, and in particular all forms of psoriasis, whether cutaneous, mucous or ungueal, and even psoriasic rheumatic, or atopical dermatitis and the different forms of eczema;

4) cutaneous disorders due to exposure to UV radiation, as well as to repair or control ageing of the skin, whether photo-induced or chronological, or to reduce pigmentations and actinic keratoses, or all pathologies associated with chronological or actinic ageing, such as xerosis, pigmentations and wrinkles;

5) Any condition associated with benign dermal or epidermal proliferations, whether or not of viral origin, such as common warts, flat warts, molluscum contagiosum and verruciform epidermodysplasia, oral or florid papillomatoses;

6) dermatological complaints such as immune dermatoses such as erythematous lupus, bullous immune diseases and collagenic diseases such as sclerodermia;

7) stigmata of epidermal and/or dermal atrophy induced by local or systemic corticosteroids, or any other form of cutaneous atrophy;

8) scarring complaints, or to prevent or repair stretch marks, or even to promote scarring;

9) any disorder of fungal origin in the cutaneous region, such as tinea pedis and tinea versicolor;

10) pigmentation disorders such as hyperpigmentation, melasma, hypopigmentation or vitiligo;

11) cancerous or pre-cancerous, cutaneous or mucous conditions such as actinic keratoses, Bowen's disease, carcinomas in-situ, keratocanthoma and skin cancers such as basocellular carcinoma (BCC), spinocellular carcinoma (SCC) (and cutaneous lymphomas such as T lymphoma.

A fourth object according to the invention relates to a method for preparing a pharmaceutical composition as described above and comprising the following stages:

a) solubilisation of the hydrophilic excipients under agitation b) solubilisation under agitation of the retinoid in the phenoxyethanol c) addition of the lipophilic excipients d) gelification of the aqueous phase by adding the polyacryl amide polymer e) addition of the oily phase then the silicone oil A fifth object according to the invention relates to the compositions comprising a compound with general formula (I)

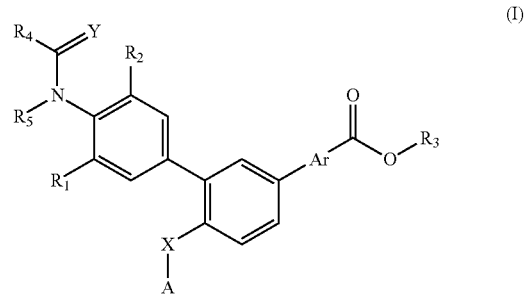

And at least one polyacryl amide gelifier, characterised in that the maximum quantity of active ingredient absorbed in the epidermis 16 hours after application, i.e. between 6 ng/cm$^2$ and 19 ng/cm$^2$.

A sixth object according to the invention relates to the compositions comprising a compound with general formula (I)

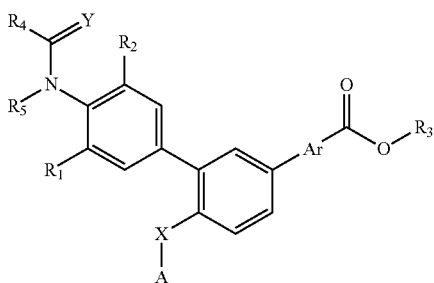

And at least polyacryl amide gelifier, characterised in that the maximum quantity of active ingredient absorbed in the epidermis is obtained between 3 and 10 hours after application.

Preferably between 5 and 7 hours after application.

A more detailed description of the invention is detailed hereafter, in the examples and in the figures

BRIEF DESCRIPTION OF THE DRAWINGS

FIG. 1 is a bar graph showing a distribution profile in the different compartments of the skin (stratum corneum, epidermis, dermis and total skin) for a reference gel of 100 μg/g of Compound A, compared to an oil in water emulsion of 100 μg/g of Compound A, where Compound A is defined above and penetration is expressed in $ng/cm^2$.

FIG. 2 is a penetration kinetics profile in the epidermis for a reference gel of 100 μg/g of Compound A and for an oil in water emulsion of 100 μg/g of Compound A, where the penetration of Compound A in $ng/cm^2$ is plotted against the time in hours.

FIG. 3 illustrates the results of a tolerance study of subjects treated with a reference gel of Compound A in comparison with subjects treated with an oil in water emulsion of Compound A (Cream B) without an emulsifying agent, where the percentage of subjects needing a change in the area of application is plotted against time in days.

DESCRIPTION OF THE INVENTION

To facilitate a reading of this description reference will be made to general formula (1) and compound A in the remaining text, as described thus:

General formula (I):

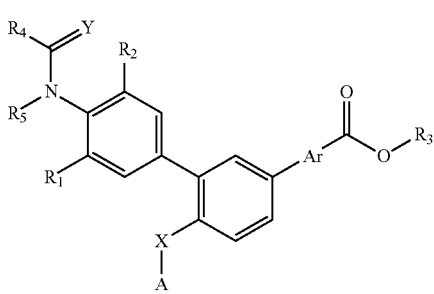

where:
$R_1$ is a hydrogen atom, an alkyl radical of 1 to 4 carbon atoms or a —$CF_3$ radical;
$R_2$ is a hydrogen atom, an alkyl or alkoxy radical of 1 to 4 carbon atoms or a chlorine atom;
$R_3$ is a hydrogen atom, an alkyl or alkoxy radical of 1 to 10 linear or branched carbon atoms, possibly substituted by a methoxy group;
$R_4$ is a hydrogen atom or an alkyl radical of 1 to 3 carbon atoms;
$R_5$ is a hydrogen atom or an alkyl radical of 1 to 3 carbon atoms;
or $R_4$ and $R_5$ together form, with the bond —N—C(=Y)—, a ring of the type pyrrolidine, pyrrolidinone, piperidine or piperidinone;
Y denotes two hydrogen atoms or one heteroatom such as oxygen or sulphur;
Ar denotes a 1,4-phenyl, 2,5-pyridyl, 5,2-pyridyl or 2,5-thiophenyl ring;
X denotes an oxygen atom, possibly substituted by an alkyl or alkyamine chain or a single C—C bond;
A denotes a hydrogen atom or the following formula:

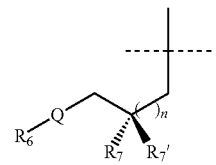

where
Q is an oxygen atom or the bond —NH—;
$R_6$ denotes a hydrogen atom, an alkyl radical of 1 to 6 carbon atoms, a cycloalkyl radical of 3 to 6 carbon atoms, a —$C(O)CH_2$ or —$C(O)CH_2CH_3$ radical;
$R_7$ and $R_7'$ denote, independently of each other, a hydrogen atom or a hydroxyl group, on condition that $R_7$ and $R_7'$ are not simultaneously a hydroxyl group;
n is equal to 0, 1, 2, 3, 4 or 5;

Compound A: as being 3"-tert-butyl-4'-(2-hydroxyethoxy)-4"-pyrrolidin-1-yl-[1,1';3',1"]-terphenyl-4-carboxylic acid.

Due to the physico-chemical characteristics of the active ingredient, we have had to face a certain number of constraints in the use of the compounds described by general formula (I). These compounds:
are soluble in few solvents normally used in the fat phases of the topical emulsions
are chemically degraded in a number of their solvents
degrade chemically in the presence of numerous emulsifiers.

A first object according to this invention describes compositions containing at least one compound with general formula (I) in the form of emulsions of the type O/W (Oil in Water) and in which the active ingredient is solubilised in the fat phase.

These emulsions exhibit good physical and chemical stability, a rapid rate of penetration and a high level of penetration in the epidermis and/or the dermis.

In a preferred mode, the composition according to the invention is without emulsifier.

Emulsion is understood to mean a macroscopically homogeneous but microscopically heterogeneous mixture of two immiscible liquid substances that we shall call phases. An O/W (oil in water) emulsion consists of a fat (or oily) phase dispersed in an aqueous phase.

In the invention the compositions contain a quantity of active ingredient described by general formula (I) at concentrations ranging from 0.00001% to 1% w/w, preferably from 0.0001 to 0.1% w/w, and more preferably from 0.001 to 0.1% w/w.

Preferably the active ingredient described by general formula (I) is compound A.

In the invention the compositions contain at least one aqueous phase gelifier used alone or in combination:

Gelling agent means agent capable of giving a composition the texture of a polymeric gel compound.

Gelling agents may be chosen from the plant polymers, gums, pectins, cellulose and its derivatives, microbiological origin polymers such as xanthan gum, gelling and synthetic polymers.

By way of non-exhaustive example of gelifiers that may enter into the compositions, mention may be made of Acrylates/C10-30 Alkyl Acrylate Cross polymer, sold under the name of Pemulen TR-1 or Pemulen TR-2 by the company Noveon, gelifiers in the polyacryl amide family, such as the mixture of Sodium acrylamide/acryloyldimethyltaurate copolymer/isohexadecane/polysorbate 80, sold under the name of Simulgel 600PHA by the company SEPPIC, and the mixture of polyacrylamide/isoparaffine C13-14/laureth-7 sold under the name of Sepigel 305 by the company SEPPIC, The carbomers sold under the name of Ultrez 20®, Ultrez 10®, Carbopol 1382® or Carbopol ETD2020NF®, Carbopol 981 or even Carbopol 980 by the company Noveon, the polysaccharides with, by way of non-exhaustive examples, xanthan gum, such as Xantura1180® sold by the company Kelco, gellan gum, solder under the name of Kelcogel by the company Kelco, guar gum, cellulose and its derivatives, such as microcrystalline cellulose and carboxymethyl cellulose of sodium sold under the name of Avicel CL-611 by the company FMC Biopolymer, hydroxypropylmethylcellulose, in particular the product sold under the name of Methocel E4M premium by the company Dow Chemical, or hydroxyethylcellulose, in particular the product sold under the name of Natrosol HHX 250® by Aqualon, sodium carboxymethylcellulose, in particular Blanose cellulose gum 7F sold by the company Aqualon, the family of aluminium magnesium silicates, such as Veegum K sold by the company Vanderbilt, the family of acrylic polymers coupled to hydrophobic chains such as PEG-150/decyl/SMDI copolymer sold under the name of Aculyn 44 (polycondensate, comprising, at least as elements, a polyethylene glycol with 150 or 180 mols of ethylene oxide, decyclic alcohol and methylene bis(4-cyclohexylisocyanate) (SMDI), at 35% by weight in a mixture of propylene glycol (39%) and water (26%)), the family of modified starches such as modified potato starch sold under the name of Structure Solanaceae or their mixtures, the family of the carrageenans, particularly those distributed among four manor families: κ, λ, β, ω, such as Viscarin® and the Gelcarin® marketed by the company IMCD.

In preference a gelifier of the polyacrylamide type, such as Simulgel 600 PHA®, which has thickening and stabilising properties, will be used in concentrations ranging from 0.005 to 5% w/w, and preferably ranging from 1% to 4% w/w, alone or associated with at least one of the above-mentioned gelifiers.

The person skilled in the art knows that for an emulsifier system the proportion of emulsifier required to emulsify a fat phase in an oil in water emulsion is normally of the order of ⅕ of a % of the fat phase. By way of non-exhaustive example a fat phase representing at least 11% of the ingredients of the formulae would require a minimum of 2.5% of emulsifiers.

In the invention, no emulsifier is used as an ingredient in our compositions. However, it is possible that certain ingredients contain low percentages of emulsifier in their own composition. Because of the low percentage that may result from this in our compositions they cannot be used as an emulsifier (lower than 0.6%).

In the invention the compositions contain a fat phase that may consist of:

a solvent of an active ingredient described by general formula (I), which may be benzyl alcohol, laureth-4, phenoxyethanol, propylene glycol monocaprylate, pentylene glycol or dimethyl isosorbide, and preferably phenoxyethanol sold under the name phenoxetol by Clariant, the quantity of phenoxyethanol being 0.2 to 5%, and preferably 0.5 to 2%.

one or more co-solvent oils which may be, in preference, the following co-solvent oils: Caprylic/capric triglycerides (Miglyol 812N) supplied by IMCD, *Prunus Amygdalus* Dulcis (Sweet Almond) oil supplied by SICTIA, Propylene glycol monocaprylate (Capryol 90) supplied by GATTEFOSSE, Propylene glycol laurate (Lauroglycol FCC) supplied by GATTEFOSSE, Sorbitan Sesquioleate (Arlacel 83VPharma) supplied by CRODA, Diisopropyl Adipate (Crodamol DA) supplied by CRODA, PPG-15 stearyl ether (Arlamol E) supplied by CRODA, Apricot Kernel Oil PEG-6 Ester (Labrafil M1944CS) supplied by GATTEFOSSE in proportions ranging from 0.5 to 50% and preferably from 4 to 30%.

In the invention the compositions described above may also contain additives (among which mention may be made of the following categories, used alone or in combination):

Silicon oils that improve the properties of the formula for the formulation, such as Cyclomethicone (St-Cyclomethicone 5NF) or Dimethicone (Q7 9120 silicon fluid, with a viscosity of 20 cst to 12500 cst from Dow Corning) between 0 and 10%, and preferably between 0 and 4%.

Preservatives such as methyl parabene, propyl parabene, benzalconium chloride, phenoxyethanol sold under the name of phenoxetol by Clariant, benzyl alcohol sold by Merck, potassium sorbate sold under the name of potassium Sorbate by VWR, benzoic acid sold under the name Benzoic Acid by VWR, 2-Bromo-2-Nitropropane-1,3-Diol sold under the name of Bronopol by Jan Dekker International, Chlorohexidine sold under the name of Chlorohexidine digluconate 20% solution by Arnaud Pharmacie, chlorocresol and its derivatives, ethyl alcohol and diazolidinyl urea. These preservatives may be used alone or in combination for effective protection of formulae against all bacterial contamination from 0% to 5%, and preferably from 0.01 to 2%.

Ethanol, the quantity of which is between 0 and 30%, preferably between 0 and 10%.

Moistening agents, preferably polyols and preferably selected from among propylene glycol, glycerine, diglycerine or sorbitol (Neosorb supplied by ROQUETTE, Parteck SI supplied by Merck, but also Sorbitol USP Powder supplied by LIPO CHEMICALS, whose quantity ranges from 0 to 40% by weight relative to the total weight of the composition, and preferably from 5 to 35%.

Chelating agents such as EDTA (ethylene diamine tetraacetic acid) and its derivatives or salts, dihydroglycerine, citric and tartaric acids, gluconolactone sold under the name D-(+)-glucono-delta-lactone by MERCK or mixtures thereof.

Antioxidants such as vitamin E and its derivatives, such as DL alpha tocopherol or tocopherol acetate from Roche; vitamin C and its derivatives, such as Ascorbyl Palmitate from Roche, Butylhydroxy toluene sold under the name of Nipanox BHT by Clariant.

Palliatives and/or anti-irritants such as PPG-12/SMDI copolymer sold by Bertek Pharmaceuticals under the commercial name of Polyolprepolymer-2, glycyrrhetinic acid or its derivatives, for example Enoxolone sold by Cognis, hyaluronic acid as such or in its form of sodium hyaluronate sold under the commercial name of HYAL. NA PWD PH 15-51-45 by Laserson, allantoin sold under the name of RONACARE ALLANTOINE by MERCK.

Any other additive normally used in the pharmaceutical and cosmetic fields enabling specific properties to be assigned to the said preparation.

General Composition for Acne:

The percentages are expressed by weight in relation to the total weight of the composition of the oil in water emulsion type.

from 0.00001% to 1% and preferably from 0.001 to 0.1% of compound with the general formula (I)
from 0.005 to 10% and preferably from 1 to 5% of gelling agent
from 0.2 to 5% and preferably from 0.5 to 2% of solvent of compound with the general formula (I)
from 0.5 to 50% and preferably from 4 to 15% of co-solvent oils of compound with the general formula (I)
from 0 to 20% and preferably from 0 to 5% of mineral oils
from 0 to 50% and preferably from 5 to 35% of polyol
from 0 to 10% and preferably from 0 to 4% of silicone oil
from 0 to 5% and preferably from 0.01 to 2% of preservative system
from 0 to 30% and preferably from 0 to 10% of ethanol
from 0 to 15% and preferably from 0.1 to 10% of additives Compositions Suitable for Ichtyosis, Palmoplantar Hyperkeratosis or Psoriasis:

The percentages are expressed by weight in relation to the total weigh of the composition of the oil in water type.

From 0.00001% to 1% and preferably from 0.001 to 0.12% of compound with the general formula (I)
from 0.005 to 10% and preferably from 1 to 5% of gelling agent
from 0.2 to 5% and preferably from 0.5 to 2% of solvent of compound with the general formula (I)
from 0.5 to 50% and preferably from 10 to 30% of co-solvent oils of compound with the general formula (I)
from 1 to 50% and preferably from 10 to 30% of polyol
from 0 to 10% and preferably from 0 to 4% of silicone oil
from 0 to 5% and preferably from 0.01 to 2% of preservative system
from 0 to 15% and preferably from 0.1 to 10% of additives Another object according to the invention relates to a method of preparing a composition described as above and comprising the following stages:

A) Preparation of the aqueous phase
Solubilisation of the hydrophilic excipients under agitation, if necessary under heat B) Preparation of the oily phase
In a suitable receptacle, solubilisation under agitation, of compound A in Phenoxyethanol, under heat if necessary.
Allow to return to ambient temperature and add the lipophilic excipients except the silicone oil (ST-cyclomethicone 5 as an example) when this oil is present in the formula to be achieved.

C) Mixing of the two phases.
At ambient temperature gelify the aqueous phase by adding Simulgel 600PHA, then add the oily phase then the ST-cyclomethicone 5.

EXAMPLES

Example 1

Pre-formulation

In order to obtain an oil in water emulsion containing a compound with the general formula (I) in the fat phase, pre-formulation studies have been conducted to provide evidence of the excipients allowing good solubilisation as well as good stability of the active ingredient.

(1) List of fat phase excipients in which the maximum solubility has been determined by HPLC:

| Excipients | | Maximum solubility |
|---|---|---|
| Commercial name | INCI name | % |
| Benzyl alcohol | Benzyl Alcohol | 2.388 |
| Brij 30 | Laureth-4 | 2.03 |
| Phenoxetol | Phenoxyethanol | 1.957 |
| Capryol 90 | Propylene glycol monocaprylate | 0.802 |
| Hydrolite 5P | Pentylene glycol | 0.482 |
| Arlasolve DMI | Dimethyl Isosorbide | 0.400 |
| Crodamol IPM | Isopropyl myristate | <0.1 |

The limit, below which the compounds of general formula (1) are considered non-solubilized, is 0.1% by weight.

(2) Stability of compound A in its principal solvents:

These stability studies of compound A in its principal solvents show that compound A degrades chemically in a number of its solvents.

These results have enabled us to select our principal solvent (phenoxyethanol) and our co-solvent oils from among the solvent oils which exhibit good stability results, with the aim of developing W/O emulsions in which compound A is solubilised in the oily phase.

| Excipients | | | |
|---|---|---|---|
| Commercial name | INCI name | COMPOUND A % | Stability results |
| Miglyol 812N | Caprylic/capric triglycerides | 0.005% | Stable/Ok 6 Months 40° C. |
| Sweet almond oil | *Prunus Amygdalus Dulcis* (Sweet Almond) Oil | 0.005% | Stable/Ok 6 Months 40° C. |

Excipients

| Commercial name | INCI name | COMPOUND A % | Stability results |
|---|---|---|---|
| Capryol 90 | Propylene glycol monocaprylate | 0.05% | Stable/Ok 6 Months 40° C. |
| Arlacel 83V Pharma | Sorbitan Sesquioleate | 0.05% | Stable/Ok 6 Months 40° C. |
| Crodamol DA | Diisopropyl Adipate | 0.05% | Stable/Ok 6 Months 40° C. |
| Lauroglycol FCC | Propylene glycol laurate | 0.05% | Stable/Ok 6 Months 40° C. |
| Arlamol E | PPG-15 stearyl ether | 0.05% | Stable/Ok 6 Months 40° C. |
| Phenoxetol | Phenoxyethanol | 0.05% | Stable/Ok 6 Months 40° C. |
| Labrafil M1944CS | Apricot Kernel Oil PEG-6 Ester | 0.05% | Stable/Ok 6 Months 40° C. |
| Dipropylene Glycol Care | Dipropylene glycol | 0.05% | Unstable |
| Brij 30 | Laureth-4 | 0.05% | Unstable |
| Benzyl Alcohol | Benzyl Alcohol | 0.05% | Unstable |
| Eutanol G | Octyldodecanol | 0.05% | Unstable |
| Myritol PC | Propylene glycol dicaprylate/dicaprate | 0.05% | Unstable |
| Arlasolve DMI | Dimethyl Isosorbide | 0.05% | Unstable |
| Marcol 152 | Parrafinum liquidum | 0.05% | Unstable |

(3) Stability of compound A in mixtures of excipients (solvent/surfactants) determined by HPLC:

Studies of stability of compound A solubilised in oils (in which it is stable) in the presence of surfactants have been conducted:

Mixture of excipients

| Commercial name | INCI name | COMPOUND A % | Stability results |
|---|---|---|---|
| Simulsol M45/Crodamol DA | PEG-8 Stearate/Diisopropyl Adipate | 0.05% | Unstable |
| Cremophor EL/Labrafil M1944CS | PEG-35 Castor Oil/Apricot Kernel Oil PEG-6 Ester | 0.05% | Unstable |
| Tween 80/Arlamol E | Polysorbate-80/PPG-15 stearyl ether | 0.05% | Unstable |
| Cremophor EL/Lauroglycol FCC | PEG-35 Castor Oil/Propylene glycol laurate | 0.05% | Unstable |
| Tween 80/Hexylene glycol | Polysorbate-80/Hexylene glycol | 0.2% | Unstable |
| Cremophor EL/Labrafil M1944CS | PEG-35 Castor Oil/Apricot Kernel Oil PEG-6 Ester | 0.2% | Unstable |
| Cremophor RH40/Crodamol DA | PEG-40 Hydrogenated Castor Oil/Diisopropyl Adipate | 0.2% | Unstable |
| Tween 80/Lauroglycol FCC | Polysorbate-80/Propylene glycol laurate | 0.2% | Unstable |
| Simulsol M45/Crodamol DA | PEG-8 Stearate/Diisopropyl Adipate | 0.2% | Unstable |
| Arlacel 165/Lauroglycol FCC | Glyceryl Stearate PEG-100 Stearate/Propylene glycol laurate | 0.05% | Unstable |
| GlucateSS-Glucamate SSE-20/Arlamol E | Methyl Glucose Sesquistearate-PEG-20 Methyl Glucose Sesquistearate/PPG-15 stearyl ether | 0.05% | Unstable |
| Brij 721/Arlamol E | Steareth-21/PPG-15 stearyl ether | 0.05% | Stable/Ok 3 Months 40° C. |
| Brij 721/Lauroglycol FCC | Steareth-21/Propylene glycol laurate | 0.05% | Stable/Ok 3 Months 40° C. |

-continued

| Mixture of excipients | | | |
|---|---|---|---|
| Commercial name | INCI name | COMPOUND A % | Stability results |
| Eumulgin B2/ Arlamol E | Ceteareth-20/PPG-15 stearyl ether | 0.05% | Stable/Ok 3 Months 40° C. |
| Arlacel 165/ Arlamol E | Glyceryl Stearate PEG-100 Stearate/PPG-15 stearyl ether | 0.05% | Stable/Ok 3 Months 40° C. |
| GlucateSS-Glucamate SSE-20/ Lauroglycol FCC | Methyl Glucose Sesquistearate-PEG-20 Methyl Glucose Sesquistearate/Propylene glycol laurate | 0.05% | Stable/Ok 3 Months 40° C. |

The limits fixed for high stability are 95%-105% as a percentage relative to T0.

These studies showed that compound A degrades chemically in the presence of numerous surfactants. Following these results we therefore decided to develop an O/W without emulsifier.

Example 2

Formulations

In the following examples the formulae are characterised at T0. The physical and chemical stability of the formulations is achieved after storage at ambient temperature (TA) and at 40° C. after T+1 Month and/or T+2 Months or T+3 Months or T+6 Months. The equipment and methods used for these characteristics are described below.

Since compound A is defined as 3"-tert-butyl-4'-(2-hydroxy-ethoxy)-4"-pyrrolidin-1-yl-[1,1';3',1"]-terphenyl-4-carboxylic acid.

Chemical Dose of Compound A:
  Equipment: HPLC
  Expression of the results: the titre of the active ingredient is expressed as a % related to the initial % achieved at T0. The limits fixed for high stability are 95%-105%.
Macroscopic Observation:
  Macroscopic observation enables the physical integrity of the products at T0 and after stability to be guaranteed.
Microscopic Observation:
  Microscopic observation enables good solubilisation of compound A from T0, non-recrystallisation in the course of time, as well as the size of the globules in the oily phase to be evaluated.
  Equipment: AXIO ZEISS Microscope
pH:
  Equipment: METTLER TOLEDO Seven Multi pH meter
  Method: Measurements carried out at ambient temperature after 24 h stabilisation in an enclosure at 25° C. of all the samples.
Viscosity
  The measurement of the viscosity enables the consistency of the formulae produced to be evaluated.
  Equipment: Brookfield RV DVII+Pro
  Method: Measurements carried out at ambient temperature after 24 h stabilisation in an enclosure at 25° C. of all the samples. The value is read after 1 minute. The choice of mobile phase and speed will be described in each composition example. The values obtained are expressed in centipoises (Cps).
Centrifuging:
  The centrifuging enables the resistance of the formulae to a mechanical stress to be evaluated.
  Equipment: Galaxy 14D VWR
  Method: 30 minutes at 5000 rpm
  A conforming result means that there is neither separation of phases nor exudate.
Formula 1

| COMMERCIAL NAME | INCI NAME | % |
|---|---|---|
| COMPOUND A | COMPOUND A | 0.010 |
| PROPYLENE GLYCOL | Propylene Glycol | 30.000 |
| ETHANOL 95-96% | Ethanol | 5.000 |
| RONACARE ALLANTOIN | Allantoln | 0.200 |
| SIMULGEL 600 PHA | Acrylamide, AMPS Copolymer Dispersion 40%/ Isohexadecane/polysorbate 80 | 3.000 |
| MIGLYOL 812 N | Medium-Chain Triglycerides | 8.000 |
| ST-CYCLOMETHICONE 5-NF | Cyclopentasiloxane | 2.000 |
| PHENOXETOL | Phenoxyethanol | 1.000 |
| PURIFIED WATER | Purified water | QSP 100.000 |
| CHARACTERISATION AT T0 | MACROSCOPIC APPEARANCE | White, smooth, brilliant cream |
| | MICROSCOPIC APPEARANCE | Absence of crystals. Very fine, homogeneous crystal. Ø < 5 µm: 90% |
| | pH | 5 |
| | VISCOSITY | Needle 6, Rate 5. 176 000 cp |
| | CENTRIFUGING | Conforming |

-continued

| | STABILITY MONITORING | | 1 Month | 2 Months | 3 Months | 6 Months |
|---|---|---|---|---|---|---|
| Physical stability | pH TA/40° C. | | 5.28/5.31 | 5.45/5.81 | 5.30/5.67 | 5.23/5.75 |
| | Viscosity | TA | 169 000 cP | 166 000 cP | 175 000 cP | 172 000 cP |
| | | 40° C. | 174 000 cP | 173 000 cP | 165 000 cP | 159 000 cP |
| Chemical stability | Dose COMPOUND A Initial % | TA | 98.70 | 100.40 | 100.30 | 103.10 |
| | | 40° C. | 99.40 | 101.30 | 98.80 | 104.90 |

Formula 2

| COMMERCIAL NAME | INCI NAME | % |
|---|---|---|
| COMPOUND A | COMPOUND A | 0.005 |
| PROPYLENE GLYCOL | Propylene Glycol | 30.000 |
| ETHANOL 95-96% | Ethanol | 5.000 |
| RONACARE ALLANTOIN | Allantoin | 0.200 |
| SIMULGEL 600 PHA | Acrylamide, AMPS Copolymer Dispersion 40%/Isohexadecane/polysorbate 80 | 3.000 |
| MIGLYOL 812 N | Medium-Chain Triglycerides | 8.000 |
| ST-CYCLOMETHICONE 5 | Cyclopentasiloxane | 2.000 |
| PHENOXETOL | Phenoxyethanol | 1.000 |
| PURIFIED WATER | Purified water | QSP 100.000 |

| CHARACTERISATION AT T0 | MACROSCOPIC APPEARANCE | White, smooth, brilliant cream | | | |
|---|---|---|---|---|---|
| | MICROSCOPIC APPEARANCE | Absence of crystals. Very fine, homogeneous emulsion. Ø < 5 μm: 90% | | | |
| | pH | 5 | | | |
| | VISCOSITY | 176 000 cP | | | |
| | CENTRIFUGING | Conforming | | | |
| Chemical stability | Dose COMPOUND A Initial % | TA | 100.60 | 100.20 | 98.00 | 100.50 |
| | | 40° C. | 99.40 | 100.40 | 96.80 | 96.60 |

Formula 3

| COMMERCIAL NAME | INCI NAME | % |
|---|---|---|
| COMPOUND A | COMPOUND A | 0.010 |
| PROPYLENE GLYCOL | Propylene Glycol | 30.000 |
| BLANOSE CELLULOSE GUM 7H4F | Cellulose Gum | 0.800 |
| ETHANOL 95-96% | Ethanol | 5.000 |
| RONACARE ALLANTOIN | Allantoin | 0.200 |
| SIMULGEL 600 PHA | Acrylamide, AMPS Copolymer Dispersion 40%/Isohexadecane/polysorbate 80 | 2.000 |
| MIGLYOL 812 N | Triglycerides Medium-Chain | 8.000 |
| ST-CYCLOMETHICONE 5 | Cyclopentasiloxane | 2.000 |
| PHENOXETOL | Phenoxyethanol | 1.000 |
| PURIFIED WATER | Purified water | QSP 100.00 |

| CHARACTERISATION AT T0 | MACROSCOPIC APPEARANCE | White, smooth, brilliant cream |
|---|---|---|
| | MICROSCOPIC APPEARANCE | Absence of crystals. Very fine, homogeneous emulsion. Ø < 5 μm: 90% |
| | pH | 6.36 |
| | VISCOSITY | Needle 6, Rate 10. 57 500 cP |
| | CENTRIFUGING | NR |

| | STABILITY MONITORING | | 1 Month | 2 Months | 3 Months | 6 Months |
|---|---|---|---|---|---|---|
| Physical stability | pH TA/40° C. | | 6.61/6.31 | 6.7/6.21 | 6.48/6.18 | 6.40/6.08 |
| | Viscosity | TA | 64 500 cP | 59 800 cP | 67 000 cP | 64 600 cP |
| | | 40° C. | 59 000 cP | 59 000 cP | 55 100 cP | 57 300 cP |
| Chemical stability | Dose COMPOUND A Initial % | TA | 104.00 | 100.5 | 100.00 | 95.00 |
| | | 40° C. | 104.8 | 100.00 | 99.60 | 94.70 |

Formula 4

| COMMERCIAL NAME | INCI NAME | % |
|---|---|---|
| COMPOUND A | COMPOUND A | 0.010 |
| PROPANEDIOL-1,2 | Propylene Glycol | 30.000 |
| ETHANOL 95-96% | Ethanol | 5.000 |
| RONACARE ALLANTOIN | Allantoin | 0.200 |

-continued

| COMMERCIAL NAME | INCI NAME | % |
|---|---|---|
| SIMULGEL 600 PHA | Acrylamide, AMPS Copolymer Dispersion 40%/Isohexadecane/polysorbate 80 | 3.000 |
| MIGLYOL 812 N | Caprylic/Capric Triglyceride | 8.000 |
| LABRAFIL M1944CS | Apricot Kernel Oil PEG-6 Ester | 2.000 |
| ST-CYCLOMETHICONE 5 | Cyclopentasiloxane | 2.000 |
| PHENOXETOL | Phenoxyethanol | 1.000 |
| PURIFIED WATER | Purified water | QSP 100.000 |

| CHARACTERISATION AT T0 | | |
|---|---|---|
| | MACROSCOPIC APPEARANCE | White, smooth, brilliant cream |
| | MICROSCOPIC APPEARANCE | Absence of crystals. Very fine, homogeneous emulsion. Ø < 5 μm: 90% |
| | pH | 4.72 |
| | VISCOSITY | Needle 6, Rate 2.5. 215 000 cP |
| | CENTRIFUGING | NR |

| | STABILITY MONITORING | | 1 Month | 2 Months | 3 Months | 6 Months |
|---|---|---|---|---|---|---|
| Physical stability | pH TA/40° C. | | NR/5.58 | NR/5.47 | NR/5.53 | NR/NR |
| | Viscosity | TA | NR | NR | NR | NR |
| | | 40° C. | 183 000 cP | 168 000 cP | 158 000 cP | NR |
| Chemical stability | Dose COMPOUND A Initial % | TA | 1.5 Months: 99.90 | | 99.90 | NR |
| | | 40° C. | 1.5 Months: 99.00 | | 99.40 | NR |

Formula 5

| COMMERCIAL NAME | INCI NAME | % |
|---|---|---|
| COMPOUND A | COMPOUND A | 0.010 |
| PROPANEDIOL-1,2 | Propylene Glycol | 30.000 |
| ETHANOL 95-96% | Ethanol | 5.000 |
| RONACARE ALLANTOIN | Allantoin | 0.200 |
| SIMULGEL 600 PHA | Acrylamide, AMPS Copolymer Dispersion 40%/Isohexadecane/polysorbate 80 | 3.000 |
| MIGLYOL 812 N | Caprylic/Capric Triglyceride | 8.000 |
| ARLAMOL PS15E-LQ (WL) | PPG-15 stearyl ether | 2.000 |
| ST-CYCLOMETHICONE 5-NF | Cyclopentasiloxane | 2.000 |
| PHENOXETOL | Phenoxyethanol | 1.000 |
| PURIFIED WATER | Purified water | QSP 100.000 |

| CHARACTERISATION AT T0 | | |
|---|---|---|
| | MACROSCOPIC APPEARANCE | White, smooth, brilliant cream |
| | MICROSCOPIC APPEARANCE | Absence of crystals. Fine, homogeneous emulsion. Ø < 10 μm: 90% |
| | pH | 4.64 |
| | VISCOSITY | Needle 6, Rate 2.5. 314 000 cP |
| | CENTRIFUGING | NR |

| | STABILITY MONITORING | | 1 Month | 2 Months | 3 Months | 6 Months |
|---|---|---|---|---|---|---|
| Physical stability | pH TA/40° C. | | NR/5.62 | NR/5.68 | NR/5.65 | NR/5.81 |
| | Viscosity | TA | NR | NR | NR | NR |
| | | 40° C. | 267 000 cP | 268 000 cP | 262 000 cP | 246 000 cP |
| Chemical stability | Dose COMPOUND A Initial % | TA | 1.5 Months: 98.80 | | 100.70 | 107.00 |
| | | 40° C. | 1.5 Months: 106.00 | | 100.70 | 107.70 |

Formula 6

| COMMERCIAL NAME | INCI NAME | % |
|---|---|---|
| COMPOUND A | COMPOUND A | 0.030 |
| PROPANEDIOL-1,2 | Propylene Glycol | 30.000 |
| ETHANOL 95-96% | Ethanol | 5.000 |
| RONACARE ALLANTOIN | Allantoin | 0.200 |

-continued

| | | |
|---|---|---|
| SIMULGEL 600 PHA | Acrylamide, AMPS Copolymer Dispersion 40%/ Isohexadecane/polysorbate 80 | 3.000 |
| ST-CYCLOMETHICONE 5NF | Cyclopentasiloxane | 2.000 |
| CASTOR OIL SEED PH | *Ricinus Communis* (Castor) Seed Oil | 8.000 |
| PHENOXETOL | Phenoxyethanol | 1.000 |
| PURIFIED WATER | Purified water | QSP 100.000 |

| | | |
|---|---|---|
| CHARACTERISATION AT T0 | MACROSCOPIC APPEARANCE | White, smooth, brilliant cream |
| | MICROSCOPIC APPEARANCE | Absence of crystals. Fine, homogeneous emulsion. Ø < 5 μm: 90% |
| | pH | 5.67 |
| | VISCOSITY | Needle 29, Rate 0.5. 1 180 000 cP |
| | CENTRIFUGING | Conforming |

| | STABILITY MONITORING | | 1 Month | 2 Months | 3 Months | 6 Months |
|---|---|---|---|---|---|---|
| Physical stability | pH TA/40° C. | | 5.66/5.55 | 5.73/5.82 | 5.44/5.84 | 5.44/5.84 |
| | Viscosity | TA | 1 160 000 cP | 1 080 000 | 1 080 000 cP | 1 080 000 cP |
| | | 40° C. | 1 130 000 cP | 1 030 000 | 1 090 000 cP | 1 030 000 cP |
| Chemical stability | Dose COMPOUND A Initial % | TA | 99.8 | 100.0 | 100.4 | 100.0 |
| | | 40° C. | 99.6 | 99.5 | 99.2 | 99.5 |

Formula 7

| COMMERCIAL NAME | INCI NAME | % |
|---|---|---|
| COMPOUND A | COMPOUND A | 0.030 |
| PROPANEDIOL-1,2 | Propylene Glycol | 30.000 |
| ETHANOL 95-96% | Ethanol | 5.000 |
| RONACARE ALLANTOIN | Allantoin | 0.200 |
| SIMULGEL 600 PHA | Acrylamide, AMPS Copolymer Dispersion 40%/ Isohexadecane/polysorbate 80 | 3.000 |
| MIGLYOL 812 N | Caprylic/Capric Triglyceride | 4.000 |
| ARLAMOL PS15E-LQ (WL) | PPG-15 stearyl ether | 4.000 |
| ST-CYCLOMETHICONE 5-NF | Cyclopentasiloxane | 2.000 |
| PHENOXETOL | Phenoxyethanol | 1.000 |
| PURIFIED WATER | Purified water | QSP 100.000 |

| | | |
|---|---|---|
| CHARACTERISATION AT T0 | MACROSCOPIC APPEARANCE | White, smooth, brilliant cream |
| | MICROSCOPIC APPEARANCE | Absence of crystals. Fine homogeneous emulsion. Ø < 5 μm: 90% |
| | pH | 5.87 |
| | VISCOSITY | Needle 29, Rate 5. 139 000 cP |
| | CENTRIFUGING | Conforming |

| | STABILITY MONITORING | | 1 Month | 2 Months | 3 Months | 6 Months |
|---|---|---|---|---|---|---|
| Physical stability | pH TA/40° C. | | 5.90/5.50 | 5.71/5.71 | 5.66/5.90 | 5.66/5.90 |
| | Viscosity | TA | 148 000 cP | 132000 cP | 134 000 cP | 132000 cP |
| | | 40° C. | 142 000 cP | 130000 cP | 137 000 cP | 130000 cP |
| Chemical stability | Dose COMPOUND A Initial % | TA | 97.8 | 109.6 | 100.7 | 100.7 |
| | | 40° C. | 100.0 | 110.2 | 100.6 | 100.2 |

Formula 8

| COMPOSITIONS | | |
|---|---|---|
| Commercial Name | INCI name | % |
| COMPOUND A | COMPOUND A | 0.010 |
| PHENOXETOL | PHENOXYETHANOL | 1.00 |

-continued

| Commercial Name | INCI name | % |
|---|---|---|
| MIGLYOL 812N | CAPRYLIC/CAPRIC TRIGLYCERIDES | 15.00 |
| CASTOR OIL PH | RICINUS COMMUNIS (CASTOR) SEED OIL | 8.00 |
| ST-CYCLOMETHICONE 5NF | Cyclopentasiloxane | 2.00 |
| Q7-9120 SILICON FLUID 350 cst | DIMETHICONE | 5.00 |
| RONACARE ALLANTOIN | ALLANTOIN | 0.200 |
| GLYCERINE 4810 VEGETABLE | GLYCERINE | 20.00 |
| SIMULGEL 600 PHA | ACRYLAMIDE, AMPS COPOLYMER DISPERSION 40%/ ISOHEXADECANE/polysorbate 80 | 3.00 |
| PURIFIED WATER | PURIFIED WATER | QSP 100.00 |

| CHARACTERISATION AT T0 | | |
|---|---|---|
| MACROSCOPIC APPEARANCE | White, smooth, brilliant cream | |
| MICROSCOPIC APPEARANCE | Absence of crystals. Fine, homogeneous emulsion. Ø 6 µm | |
| pH | 4.92 | |
| VISCOSITY | Needle 6, Rate 0.5 NR | |
| CENTRIFUGING | Conforming | |

| Stability monitoring | | 1 MONTH | 2 MONTHS | 3 MONTHS | 6 MONTHS |
|---|---|---|---|---|---|
| Physical stability | pH TA/40° C. | 4.92/4.88 | NR | 4.93/5.22 | / |
| | Viscosity TA | 192·10⁴ cp | NR | 182·10⁴ cp | / |
| | 40° C. | 187·10⁴ cp | NR | 167·10⁴ cp | / |

Formula 9

| COMPOSITIONS | | |
|---|---|---|
| Commercial Name | INCI name | % |
| COMPOUND A | COMPOUND A | 0.010 |
| PHENOXETOL | PHENOXYETHANOL | 1.00 |
| MIGLYOL 812N | CAPRYLIC//CAPRIC TRIGLYCERIDES | 8.00 |
| ARLAMOL PS15E-LQ | PPG-15 STEARYL ETHER | 15.00 |
| ST-CYCLOMETHICONE 5NF | Cyclopentasiloxane | 2.00 |
| RONACARE ALLANTOIN | ALLANTOIN | 0.200 |
| GLYCERINE 4810 VEGETABLE | Glycerine | 20.00 |
| SIMULGEL 600 PHA | ACRYLAMIDE, AMPS COPOLYMER DISPERSION 40%/ ISOHEXADECANE/polysorbate 80 | 2.5 |
| PURIFIED WATER | PURIFIED WATER | QSP 100.00 |

| CHARACTERISATION AT T0 | | |
|---|---|---|
| MACROSCOPIC APPEARANCE | White, smooth, brilliant cream | |
| MICROSCOPIC APPEARANCE | Absence of crystals. Fine, homogeneous emulsion. Ø < 7 µm | |
| pH | 4.79 | |
| VISCOSITY | Needle 6, Rate 5 187000 cp | |
| CENTRIFUGING | RAS | |

| Stability monitoring | | 1 MONTH | 2 MONTHS | 3 MONTHS | 6 MONTHS |
|---|---|---|---|---|---|
| Physical stability | pH TA/40° C. | 4.76/4.87 | 4.92/4.99 | 4.83/5.08 | 4.59/5.13 |
| | Viscosity TA | 160000 cp | 175000 cp | 186000 cp | 132000 cP |
| | 40° C. | 154000 cp | 146000 cp | 146000 cp | 137000 cP |

Formula 10

| COMPOSITIONS | | |
|---|---|---|
| Commercial Name | INCI name | % |
| COMPOUND A | COMPOUND A | 0.030 |
| PHENOXETOL | PHENOXYETHANOL | 1.00 |

-continued

| Commercial Name | INCI name | % |
|---|---|---|
| MIGLYOL 812N | CAPRYLIC//CAPRIC TRIGLYCERIDES | 8.00 |
| ARLAMOL PS15E-LQ | PPG-15 STEARYL ETHER | 15.00 |
| ST-CYCLOMETHICONE 5NF | Cyclopentasiloxane | 2.00 |
| RONACARE ALLANTOIN | ALLANTOIN | 0.200 |
| GLYCERINE 4810 VEGETABLE | Glycerine | 20.00 |
| SIMULGEL 600 PHA | ACRYLAMIDE, AMPS COPOLYMER DISPERSION 40%/ISOHEXADECANE/polysorbate 80 | 2.5 |
| PURIFIED WATER | PURIFIED WATER | QSP 100.00 |

| CHARACTERISATION AT T0 | | |
|---|---|---|
| | MACROSCOPIC APPEARANCE | White, smooth, brilliant cream |
| | MICROSCOPIC APPEARANCE | Absence of crystals. Fine, homogeneous emulsion. Ø < 7 μm |
| | pH | 4.76 |
| | VISCOSITY | Needle 6, Rate 2.5 381000 cp |
| | CENTRIFUGING | RAS |

| Stability monitoring | | 1 MONTH | 2 MONTHS | 3 MONTHS | 6 MONTHS |
|---|---|---|---|---|---|
| Physical stability | pH TA/40° C. | 4.74/4.97 | 4.88/5.00 | 4.85/5.16 | 4.96/5.12 |
| | Viscosity TA | 374000 cp | 364000 cp | 334000 cp | 298000 cP |
| | 40° C. | 288000 cp | 266000 cp | 269000 cp | 260000 cP |

Formula 11

| COMPOSITIONS | | |
|---|---|---|
| Commercial Name | INCI name | % |
| COMPOUND A | COMPOUND A | 0.04 |
| PHENOXETOL | PHENOXYETHANOL | 1.00 |
| MIGLYOL 812N | CAPRYLIC//CAPRIC TRIGLYCERIDES | 8.00 |
| ARLAMOL PS15E-LQ | PPG-15 STEARYL ETHER | 15.00 |
| ST-CYCLOMETHICONE 5NF | Cyclopentasiloxane | 2.00 |
| RONACARE ALLANTOIN | ALLANTOIN | 0.200 |
| GLYCERINE 4810 VEGETABLE | Glycerine | 20.00 |
| SIMULGEL 600 PHA | ACRYLAMIDE, AMPS COPOLYMER DISPERSION 40%/ISOHEXADECANE/polysorbate 80 | 2.5 |
| PURIFIED WATER | PURIFIED WATER | QSP 100.00 |

| CHARACTERISATION AT T0 | | |
|---|---|---|
| | MACROSCOPIC APPEARANCE | White, smooth, brilliant cream |
| | MICROSCOPIC APPEARANCE | Absence of crystals. Fine, homogeneous emulsion. Ø < 5 μm |
| | pH | 4.76 |
| | VISCOSITY | Needle 6, Rate 2.5 340000 cp |
| | CENTRIFUGING | RAS |

| Stability monitoring | | 1 MONTH | 2 MONTHS | 3 MONTHS | 6 MONTHS |
|---|---|---|---|---|---|
| Physical stability | pH TA/40° C. | 4.77/4.90 | 4.92/5.02 | 5.20/5.15 | / |
| | Viscosity TA | 343000 cp | 330000 cp | 325000 cp | / |
| | 40° C. | 292000 cp | 263000 cp | 271000 cp | / |

Formula 12

| COMPOSITIONS | | |
|---|---|---|
| Commercial Name | INCI name | % |
| COMPOUND A | COMPOUND A | 0.05 |
| PHENOXETOL | PHENOXYETHANOL | 1.00 |
| MIGLYOL 812N | CAPRYLIC//CAPRIC TRIGLYCERIDES | 8.00 |

-continued

| Commercial Name | INCI name | % |
|---|---|---|
| ARLAMOL PS15E-LQ | PPG-15 STEARYL ETHER | 15.00 |
| ST-CYCLOMETHICONE 5NF | Cyclopentasiloxane | 2.00 |
| RONACARE ALLANTOIN | ALLANTOIN | 0.200 |
| GLYCERINE 4810 VEGETABLE | Glycerine | 20.00 |
| SIMULGEL 600 PHA | ACRYLAMIDE, AMPS COPOLYMER DISPERSION 40%/ISOHEXADECANE/polysorbate 80 | 2.50 |
| PURIFIED WATER | PURIFIED WATER | QSP 100.00 |

| CHARACTERISATION TO T0 | | |
|---|---|---|
| MACROSCOPIC APPEARANCE | White, smooth, brilliant cream | |
| MICROSCOPIC APPEARANCE | Absence of crystals. Fine, homogeneous emulsion. Ø < 6 μm | |
| pH | 4.92 | |
| VISCOSITY | Needle 6, Rate 2.5 363000 cp | |
| CENTRIFUGING | RAS | |

| Stability monitoring | | 1 MONTH | 2 MONTHS | 3 MONTHS | 6 MONTHS |
|---|---|---|---|---|---|
| Physical stability | pH TA/40° C. | 4.93/4.88 | 4.79/4.93 | 4.87/5.12 | / |
| | Viscosity TA | 334000 cp | 356000 cp | 346000 cp | / |
| | 40° C. | 298000 cp | 282000 cp | 275000 cp | / |

Formula 13

| COMPOSITIONS | | |
|---|---|---|
| Commercial Name | INCI name | % |
| COMPOUND A | COMPOUND A | 0.01 |
| PHENOXETOL | PHENOXYETHANOL | 1.00 |
| MIGLYOL 812N | CAPRYLIC//CAPRIC TRIGLYCERIDES | 8.00 |
| ARLAMOL PS15E-LQ | PPG-15 STEARYL ETHER | 15.00 |
| ST-CYCLOMETHICONE 5NF | Cyclopentasiloxane | 2.00 |
| RONACARE ALLANTOIN | ALLANTOIN | 0.200 |
| GLYCERINE 4810 VEGETABLE | Glycerine | 20.00 |
| SIMULGEL 600 PHA | ACRYLAMIDE, AMPS COPOLYMER DISPERSION 40%/ISOHEXADECANE/polysorbate 80 | 3.00 |
| BENZYL ALCOHOL | BENZYL ALCOHOL | 0.40 |
| SORBATE DE POTASSIUM | POTASSIUM SORBATE | 0.10 |
| PURIFIED WATER | PURIFIED WATER | QSP 100.00 |

| CHARACTERISATION AT T0 | | |
|---|---|---|
| MACROSCOPIC APPEARANCE | White, smooth, brilliant cream | |
| MICROSCOPIC APPEARANCE | Absence of crystals. Fine, homogeneous emulsion. Ø < 5 μm | |
| pH | 6.64 | |
| VISCOSITY | Needle 6, Rate 5 147000 cp | |
| CENTRIFUGING | RAS | |

| Stability monitoring | | 1 MONTH | 2 MONTHS | 3 MONTHS | 6 MONTHS |
|---|---|---|---|---|---|
| Physical stability | pH TA/40° C. | 6.37/6.36 | 6.60/6.22 | 6.40/6.13 | / |
| | Viscosity TA | 160000 cp | 157000 cp | 121000 cp | / |

Formula 14

| COMPOSITIONS | | |
|---|---|---|
| Commercial Name | INCI name | % |
| COMPOUND A | COMPOUND A | 0.01 |
| PHENOXETOL | PHENOXYETHANOL | 1.00 |

-continued

| Commercial Name | INCI name | % |
|---|---|---|
| MIGLYOL 812N | CAPRYLIC//CAPRIC TRIGLYCERIDES | 8.00 |
| ARLAMOL PS15E-LQ | PPG-15 STEARYL ETHER | 15.00 |
| ST-CYCLOMETHICONE 5NF | Cyclopentasiloxane | 2.00 |
| RONACARE ALLANTOIN | ALLANTOIN | 0.200 |
| GLYCERINE 4810 VEGETABLE | Glycerine | 20.00 |
| SIMULGEL 600 PHA | ACRYLAMIDE, AMPS COPOLYMER DISPERSION 40%/ISOHEXADECANE/polysorbate 80 | 3.00 |
| SODIUM BENZOATE | SODIUM BENZOATE | 0.20 |
| D-(+)-GLUCONO-DELTA-LACTONE | GLUCONOLACTONE | 0.25 |
| PURIFIED WATER | PURIFIED WATER | QSP 100.00 |

| CHARACTERISATION AT T0 | | |
|---|---|---|
| MACROSCOPIC APPEARANCE | White, smooth, brilliant cream | |
| MICROSCOPIC APPEARANCE | Absence of crystals. Fine, homogeneous emulsion. Ø < 8 µm | |
| pH | 5.44 | |
| VISCOSITY | Needle 6, Rate 20 36450 cp | |
| CENTRIFUGING | RAS | |

| Stability monitoring | | 1 MONTH | 2 MONTHS | 3 MONTHS | 6 MONTHS |
|---|---|---|---|---|---|
| Physical stability | pH TA/40° C. | 4.59/4.58 | 4.70/4.78 | NR | NR |

Formula 15

| COMPOSITIONS | | |
|---|---|---|
| Commercial Name | INCI name | % |
| COMPOUND A | COMPOUND A | 0.01 |
| PHENOXETOL | PHENOXYETHANOL | 1.00 |
| MIGLYOL 812N | CAPRYLIC//CAPRIC TRIGLYCERIDES | 8.00 |
| ARLAMOL PS15E-LQ | PPG-15 STEARYL ETHER | 15.00 |
| ST-CYCLOMETHICONE 5NF | Cyclopentasiloxane | 2.00 |
| RONACARE ALLANTOIN | ALLANTOIN | 0.200 |
| GLYCERINE 4810 VEGETABLE | Glycerine | 20.00 |
| SIMULGEL 600 PHA | ACRYLAMIDE, AMPS COPOLYMER DISPERSION 40%/ISOHEXADECANE/polysorbate 80 | 3.00 |
| BENZYL ALCOHOL | BENZYL ALCOHOL | 0.80 |
| POTASSIUM SORBATE | POTASSIUM SORBATE | 0.20 |
| TITRIPLEX III | DISODIUM EDTA | 0.10 |
| PURIFIED WATER | PURIFIED WATER | QSP 100.00 |

| CHARACTERISATION AT T0 | | |
|---|---|---|
| MACROSCOPIC APPEARANCE | White, smooth, brilliant cream | |
| MICROSCOPIC APPEARANCE | Absence of crystals. Fine, homogeneous emulsion. Ø < 6 µm | |
| pH | 6.34 | |
| VISCOSITY | Needle 5, Rate 5 67920 cp | |
| CENTRIFUGING | RAS | |

Formula 16

| COMPOSITIONS | | |
|---|---|---|
| Commercial Name | INCI name | % |
| COMPOUND A | COMPOUND A | 0.01 |
| PHENOXETOL | PHENOXYETHANOL | 1.00 |
| MIGLYOL 812N | CAPRYLIC//CAPRIC TRIGLYCERIDES | 8.00 |
| ARLAMOL PS15E-LQ | PPG-15 STEARYL ETHER | 15.00 |
| ST-CYCLOMETHICONE 5NF | Cyclopentasiloxane | 2.00 |
| RONACARE ALLANTOIN | ALLANTOIN | 0.200 |
| GLYCERINE 4810 VEGETABLE | Glycerine | 20.00 |
| SIMULGEL 600 PHA | ACRYLAMIDE, AMPS COPOLYMER DISPERSION 40%/ISOHEXADECANE/polysorbate 80 | 3.00 |
| BENZOIC ACID | BENZOIC ACID | 0.20 |
| POTASSIUM SORBATE | POTASSIUM SORBATE | 0.20 |
| TITRIPLEX III | DISODIUM EDTA | 0.10 |
| PURIFIED WATER | PURIFIED WATER | QSP 100.00 |

| CHARACTERISATION AT T0 | | |
|---|---|---|
| MACROSCOPIC APPEARANCE | White, smooth, brilliant cream | |
| MICROSCOPIC APPEARANCE | Absence of crystals. Fine, homogeneous emulsion. Ø < 10 µm | |
| pH | 5.43 | |
| VISCOSITY | Needle 5, Rate 5 59520 cp | |
| CENTRIFUGING | RAS | |

Formula 17

| COMPOSITIONS | | |
|---|---|---|
| Commercial Name | INCI name | % |
| COMPOUND A | COMPOUND A | 0.01 |
| PHENOXETOL | PHENOXYETHANOL | 1.00 |

-continued

| | | | |
|---|---|---|---|
| MIGLYOL 812N | CAPRYLIC//CAPRIC TRIGLYCERIDES | | 8.00 |
| ARLAMOL PS15E-LQ | PPG-15 STEARYL ETHER | | 15.00 |
| ST-CYCLOMETHICONE 5NF | Cyclopentasiloxane | | 2.00 |
| RONACARE ALLANTOIN | ALLANTOIN | | 0.200 |
| GLYCERINE 4810 VEGETABLE | Glycerine | | 20.00 |
| SIMULGEL 600 PHA | ACRYLAMIDE,AMPS COPOLYMER DISPERSION 40%/ ISOHEXADECANE/polysorbate 80 | | 2.5 |
| BENZALCONUM CHLORIDE | BENZALKONIUM CHLORIDE | | 0.05 |
| PURIFIED WATER | PURIFIED WATER | | 5.00 |
| POTASSIUM SORBATE | POTASSIUM SORBATE | | 0.20 |
| PURIFIED WATER | PURIFIED WATER | | QSP 100.00 |
| CHARACTERISATION AT T0 | MACROSCOPIC APPEARANCE | White, smooth, brilliant cream | |
| | MICROSCOPIC APPEARANCE | Absence of crystals. Fine, homogeneous emulsion. Ø < 7 µm | |
| | pH | 6.82 | |
| | VISCOSITY | Needle 6, Rate 50 11520 cp | |
| | CENTRIFUGING | RAS | |

| | STABILITY MONITORING | | 1 Month | 2 Months | 3 Months | 6 Months |
|---|---|---|---|---|---|---|
| Physical stability | pH TA/40° C. | | 6.60/6.43 | 6.80/6.34 | 6.61/6.24 | 6.54/6.23 |
| | Viscosity | TA | 11080 cp | 10200 cp | 11200 cp | 9680 cp |
| | | 40° C. | 11760 cp | 11400 cp | 10720 cp | 9520 cp |
| Chemical stability | Dose COMPOUND A initial % | TA | 98.6 | 100.3 | 99.7 | 99.2 |
| | | 40° C. | 97 | 98.1 | 97.4 | 95.4 |

Formula 18

| COMPOSITIONS | | |
|---|---|---|
| Commercial Name | INCI name | % |
| COMPOUND A | COMPOUND A | 0.04 |
| PHENOXETOL | PHENOXYETHANOL | 1.00 |
| MIGLYOL 812N | CAPRYLIC//CAPRIC TRIGLYCERIDES | 8.00 |
| ARLAMOL PS15E-LQ | PPG-15 STEARYL ETHER | 15.00 |
| ST-CYCLOMETHICONE 5NF | Cyclopentasiloxane | 2.00 |
| RONACARE ALLANTOIN | ALLANTOIN | 0.20 |
| GLYCERINE 4810 | Glycerine | 20.00 |
| SIMULGEL 600 PHA | ACRYLAMIDE, AMPS COPOLYMER DISPERSION 40%/ ISOHEXADECANE/polysorbate 80 | 2.5 |
| BENZALCONIUM CHLORIDE | BENZALKONIUM CHLORIDE | 0.05 |
| PURIFIED WATER | PURIFIED WATER | 5.00 |
| SORBATE DE POTASSIUM | POTASSIUM SORBATE | 0.20 |
| PURIFIED WATER | PURIFIED WATER | QSP 100.00 |

| CHARACTERISATION AT T0 | MACROSCOPIC APPEARANCE | White, smooth, brilliant cream |
|---|---|---|
| | MICROSCOPIC APPEARANCE | Absence of crystals. Fine, homogeneous emulsion. Ø < 7 µm |
| | pH | 6.80 |
| | VISCOSITY | Needle 6, Rate 50 10920 cp |
| | CENTRIFUGING | RAS |

| | STABILITY MONITORING | | 1 Month | 2 Months | 3 Months | 6 Months |
|---|---|---|---|---|---|---|
| Physical stability | pH TA/40° C. | | 6.63/6.37 | 6.67/6.22 | 6.62/6.25 | 6.61/6.28 |
| | Viscosity | TA | 13340 cp | 10450 cp | 10540 cp | 10840 cp |
| | | 40° C. | 11040 cp | NR | 10400 cp | 9240 cp |

| Chemical stability | Dose COMPOUND A initial % | TA 40° C. | 100.2 99.9 | 98.3 97.5 | 99.8 99.0 | 99.4 96.8 |
|---|---|---|---|---|---|---|

Formula 19

COMPOSITIONS

| Commercial Name | INCI name | % |
|---|---|---|
| COMPOUND A | COMPOUND A | 0.01 |
| PHENOXETOL | PHENOXYETHANOL | 1.00 |
| MIGLYOL 812N | CAPRYLIC/CAPRIC TRIGLYCERIDES | 8.00 |
| ARLAMOL PS15E-LQ | PPG-15 STEARYL ETHER | 15.00 |
| ST-CYCLOMETHICONE 5NF | CYCLOPENTASILOXANE | 2.00 |
| RONACARE ALLANTOIN | ALLANTOIN | 0.20 |
| GLYCERINE 4810 VEGETABLE | GLYCERIN | 10.00 |
| SIMULGEL 600 PHA | ACRYLAMIDE, AMPS COPOLYMER DISPERSION 40%/ISOHEXADECANE/POLYSORBATE 80 | 3.00 |
| GLUCONO-DELTA-LACTONE SG | GLUCONOLACTONE | 0.25 |
| PROBENZ SP | SODIUM BENZOATE | 0.20 |
| PROPYLENE GLYCOL | PROPYLENE GLYCOL | 10.00 |
| PURIFIED WATER | PURIFIED WATER | QSP 100.00 |
| CHARACTERISATION AT T0 | MACROSCOPIC APPEARANCE | White, smooth, brilliant cream |
| | MICROSCOPIC APPEARANCE | Absence of crystals. Fine, homogeneous emulsion. |
| | pH | 6.80 |
| | VISCOSITY | Needle 6, Rate 10 59200 cp |
| | CENTRIFUGING | RAS |

Formula 20

COMPOSITIONS

| Commercial Name | INCI name | % |
|---|---|---|
| COMPOUND A | COMPOUND A | 0.01 |
| PHENOXETOL | PHENOXYETHANOL | 1.00 |
| MIGLYOL 812N | CAPRYLIC/CAPRIC TRIGLYCERIDES | 8.00 |
| ARLAMOL PS15E-LQ | PPG-15 STEARYL ETHER | 15.00 |
| ST-CYCLOMETHICONE 5NF | CYCLOPENTASILOXANE | 2.00 |
| RONACARE ALLANTOIN | ALLANTOIN | 0.20 |
| GLYCERINE 4810 VEGETABLE | GLYCERIN | 13.00 |
| SIMULGEL 600 PHA | ACRYLAMIDE, AMPS COPOLYMER DISPERSION 40%/ISOHEXADECANE/POLYSORBATE 80 | 3.00 |
| GLUCONO-DELTA-LACTONE SG | GLUCONOLACTONE | 0.25 |
| BENZYL ALCOHOL | BENZYL ALCOHOL | 1.00 |
| PROBENZ SP | SODIUM BENZOATE | 0.20 |
| PROPYLENE GLYCOL | PROPYLENE GLYCOL | 7.00 |
| PURIFIED WATER | PURIFIED WATER | QSP 100.00 |
| CHARACTERISATION AT T0 | MACROSCOPIC APPEARANCE | White, smooth, brilliant cream |
| | MICROSCOPIC APPEARANCE | Absence of crystals. Fine, homogeneous emulsion |
| | pH | 4.89 |
| | VISCOSITY | Needle 29, Rate 20 29650 cp |
| | CENTRIFUGING | RAS |

Formula 21

COMPOSITIONS

| Commercial Name | INCI name | % |
|---|---|---|
| COMPOUND A | COMPOUND A | 0.01 |
| PHENOXETOL | PHENOXYETHANOL | 1.00 |
| MIGLYOL 812N | CAPRYLIC/CAPRIC TRIGLYCERIDES | 8.00 |
| ARLAMOL PS15E-LQ | PPG-15 STEARYL ETHER | 15.00 |
| ST-CYCLOMETHICONE 5NF | CYCLOPENTASILOXANE | 2.00 |
| RONACARE ALLANTOIN | ALLANTOIN | 0.20 |
| GLYCERINE 4810 VEGETABLE | GLYCERIN | 15.00 |
| SIMULGEL 600 PHA | ACRYLAMIDE, AMPS COPOLYMER DISPERSION 40%/ISOHEXADECANE/POLYSORBATE 80 | 3.00 |
| GLUCONO-DELTA-LACTONE SG | GLUCONOLACTONE | 0.25 |
| ALCOOL BENZYLIQUE | BENZYL ALCOHOL | 1.00 |
| PROBENZ SP | SODIUM BENZOATE | 0.20 |
| PROPYLENE GLYCOL | PROPYLENE GLYCOL | 5.00 |
| PURIFIED WATER | PURIFIED WATER | QSP 100.00 |
| CHARACTERISATION AT T0 | MACROSCOPIC APPEARANCE | White, smooth, brilliant cream |
| | MICROSCOPIC APPEARANCE | Absence of crystals. Fine, homogeneous emulsion |
| | pH | 4.82 |
| | VISCOSITY | Needle 29, Rate 12 48583 cp |
| | CENTRIFUGING | RAS |

Formula 22

COMPOSITIONS

| Commercial Name | INCI name | % |
|---|---|---|
| COMPOUND A | COMPOUND A | 0.01 |
| PHENOXETOL | PHENOXYETHANOL | 1.00 |
| MIGLYOL 812N | CAPRYLIC/CAPRIC TRIGLYCERIDES | 8.00 |
| ARLAMOL PS15E-LQ | PPG-15 STEARYL ETHER | 15.00 |
| ST-CYCLOMETHICONE 5NF | CYCLOPENTASILOXANE | 2.00 |
| RONACARE ALLANTOIN | ALLANTOIN | 0.20 |
| TITRIPLEX III | EDTA | 0.20 |
| GLYCERINE 4810 VEGETABLE | GLYCERIN | 20.00 |
| SIMULGEL 600 PHA | ACRYLAMIDE, AMPS COPOLYMER DISPERSION 40%/ISOHEXADECANE/POLYSORBATE 80 | 2.50 |

-continued

| GLUCONO-DELTA-LACTONE SG | GLUCONOLACTONE | 0.25 |
| ALCOOL BENZYLIQUE | BENZYL ALCOHOL | 1.00 |
| PROBENZ SP | SODIUM BENZOATE | 0.20 |
| PURIFIED WATER | PURIFIED WATER | QSP 100.00 |
| CHARACTERISATION AT T0 | MACROSCOPIC APPEARANCE | White, smooth, brilliant cream |
| | MICROSCOPIC APPEARANCE | Absence of crystals. Fine, homogeneous emulsion |
| | pH | 4.97 |
| | VISCOSITY | Needle 29, Rate 20 29500 cp |
| | CENTRIFUGING | RAS |

Formula 23

| COMPOSITIONS | | |
| --- | --- | --- |
| Commercial Name | INCI name | % |
| COMPOUND A | COMPOUND A | 0.06 |
| PHENOXETOL | PHENOXYETHANOL | 1.00 |
| MIGLYOL 812N | CAPRYLIC/CAPRIC TRIGLYCERIDES | 8.00 |
| ARLAMOL PS15E-LQ | PPG-15 STEARYL ETHER | 15.00 |
| ST-CYCLOMETHICONE 5NF | CYCLOPENTASILOXANE | 2.00 |
| RONACARE ALLANTOIN | ALLANTOIN | 0.20 |
| GLYCERINE 4810 VEGETABLE | GLYCERIN | 20.00 |
| SIMULGEL 600 PHA | ACRYLAMIDE, AMPS COPOLYMER DISPERSION 40%/ISOHEXADECANE/POLYSORBATE 80 | 2.50 |
| CHLORURE DE BENZALKONIUM | BENZALKONIUM CHLORIDE | 0.05 |
| SORBATE DE POTASSIUM | POTASSIUM SORBATE | 0.20 |
| EAU PURIFIEE | PURIFIED WATER | QSP 100.00 |
| CHARACTERISATION TO T0 | MACROSCOPIC APPEARANCE | White, smooth, brilliant cream |
| | MICROSCOPIC APPEARANCE | Absence of crystals. Fine, homogeneous emulsion |
| | pH | 6.64 |
| | VISCOSITY | Needle 5, Rate 10 32320 cp |

| | CENTRIFUGING RAS | | | | |
| --- | --- | --- | --- | --- | --- |
| STABILITY MONITORING | | 1 Month | 2 Months | 3 Months | 6 Months |
| Physical stability | pH TA/40° C. | 6.58/6.41 | 6.44/6.23 | NR | 6.48/6.17 |
| | Viscosity TA Needle 5 Rate 1 | 309000 cp | 251000 cp | 287000 cp | 300000 cp |
| | Viscosity 40° C. Needle 5 Rate 1 | 320000 cp | 374000 cp | 324000 cp | 317000 cp |

Example 3

Characterisation of the Formulations by Cutaneous Penetration Studies on Human Skin The cutaneous penetration studies enable the formulations to be characterised and the parameters peculiar to each of the formulations to be demonstrated.

Two types of cutaneous penetration studies were carried out ex vivo on human skin. In these studies compound A corresponds to 3"-tert-butyl-4'-(2-hydroxy-ethoxy)-4"-pyrrolidin-1-yl-[1,1';3',1"]-terphenyl-4-carboxylic acid.

The reference gel is described as follows:

| Constituents | % |
| --- | --- |
| COMPOUND A | 0.01 |
| Propylene Glycol | 30.00 |
| Ethanol 95-96% | 67.99 |
| Klucel HF Pharma | 2.00 |

"Single Time" Cutaneous Penetration Study:

In this study the Formula is applied for 16 hours to the surface of the skin. After the application COMPOUND A is quantified in the different compartments of the skin: stratum corneum, epidermis, dermis and receiving liquid according to the validated bioanalysis method.

The details of the cutaneous application are given in the table below.

| Skin: 3 donors, 2 samples per donor | |
| --- | --- |
| Source | Entire abdominal human skin |
| Thickness | 0.79-1.22 mm |
| Age | 39-64 years. |
| Franz cells | 2 cm$^2$ |
| Volume of receiving liquid | 3 mL |
| Barrier function | Evaluated by determination of the Insensitive Loss in Water, acceptable except where contraindicated |

| Formulations | |
| --- | --- |
| A: Reference gel containing 100 μg/g of COMPOUND A | B: Oil in water emulsion with emulsifier, containing 100 μg/g of COMPOUND A (Formula 3) |

| Application | |
| --- | --- |
| Application | ~2 mg/cm$^2$ |
| Quantity of active ingredient applied | 142~241 ng/cm$^2$ |
| Exposure time | 16 h |

| Samples taken | | |
|---|---|---|
| Donor compartment lavage<br>Kleenex (enabling the surplus product to be removed)<br>1$^{st}$ strip | "Excess"/Unabsorbed dose | Mass balance |
| Stratum corneum (2-15 strips max)<br>Epidermis<br>Dermis | Total skin | Total penetration |
| Receiving Liquid | Absorbed dose | |

The bioanalysis was conducted by mass spectrometry in tandem by positive electrospray ionisation using a Xevo device (Waters). The limit of quantification for compound A is 1 ng/mL.

The conditions of LC/MS/MS developed enabled up to 0.1% of the doe applied in each of the compartments to be detected (unabsorbed dose, stratum, epidermis, dermis and receiving liquid).

The technical conditions are given in the table below.

| LC column | Hypersil gold 50 * 2.1 mm (UPLC) | | | | | | |
|---|---|---|---|---|---|---|---|
| Mobile phase | Phase A: ACN + 0.1% Formic Acid<br>Phase B: H$_2$O + 0.1% Formic acid | | | | | | |
| Lavage Needle | CAN | | | | | | |
| Lavage septum | ACN/H$_2$O 50:50 | | | | | | |
| Gradient | Time (min) | flow rate | % A | % B | Curve | | |
| | 1. Initial | 0.700 | 15.0 | 85.0 | 0 | | |
| | 2. 2.5 | 0.700 | 90.0 | 10.0 | 6 | | |
| | 3. 3.20 | 0.700 | 90.0 | 10.0 | 6 | | |
| | 4. 3.25 | 0.700 | 15.0 | 85.0 | 6 | | |
| Temperature of columns | | | | | | | |
| MSMS detection | ESI+ MRM (Positive electrospray)<br>Canal Reaction | Dwell (secs) | Voltage (cone) | Col. Energy | Tr (min) | COMPOUND | |
| | 1: 460.26 > 318.20 | 0.100 | 50.0 | 40.0 | 1.58 | COMPOUND A | |
| | 1: 464.06 > 372.10 | 0.100 | 55.0 | 40.0 | 1.58 | Deuterated Internal Standard | |
| Volume Injection | 5 μL | | | | | | |
| Run time | 4 minutes | | | | | | |

In this type of "single point" study the parameters considered are:
 a. The distribution profile in the different compartments (qualitative data)
 b. The penetration in the epidermis+dermis compartment (numerical data)

FIG. 1

The distribution profile between the different compartments is of the same time for the 2 formulae evaluated: accumulation in the stratum corneum, lower rate of precipitation in the epidermis, and very low penetration in the dermis. Compound A is not detected in the receiving liquid.

Penetration values in the epidermis+dermis compartment:
 The penetration values for the oil in water type emulsion without emulsifier, containing 100 μg/g (0.01%) of compound A are between 6.8 ng/cm$^2$ and 10.6 ng/cm$^2$. The levels of penetration of compound A after application of the oil in water type emulsion without emulsifier tend to be higher than those obtained after application of the reference gel.

Penetration Kinetics Study:

In this type of study the penetration of the active ingredient is quantified in each compartment of the skin after 0.5 h, 1 h, 3 h, 6 h and 24 h of application. The penetration kinetics in each compartment are then determined and characterised.

The details of the cutaneous application are given in the table below:

| | |
|---|---|
| Skin | 3 donors, 2 samples per donor per time, n = 6 |
| Source | Abdominal human skin dermatomed from corpse |
| Thickness | 500 μm |
| Age | Not Indicated |
| Franz cells | 1-2 cm$^2$ |
| Volume of Receiving Liquid | Not Indicated |
| Barrier Function | Evaluated by tritiated water |
| Products | |
| Reference gel 100 μg/g | Oil in water type emulsion without emulsifier 100 μg/g (Formula 1) |
| Formula Application | ~2 mg/cm$^2$ |
| Quantity of active ingredient applied | Between 100-200 ng/cm$^2$ |
| Exposure time | Up to 24 h |
| Samples taken | |
| Exposure time | 0.5, 1, 3, 6, 24 h |
| Lavage of donor compartment Kleenex (enabling the surplus product to be removed) 1$^{st}$ strip | "Excess"/Unabsorbed dose |
| Stratum corneum (2-15 strips max) Epidermis Dermis | Total Skin (Mass balance) |
| Analyses | LC/UV and LC/MS |
| Limit of quantification | 1 ng/ml |

The quantity of active ingredient in each compartment at each time was determined by LC/UV or by LC/MS. The bioanalysis method was validated so that at least 0.1% of the dose applied in each compartment could be detected.

In this type of study the parameters considered are:
c. The penetration kinetics profile in the epidermis (qualitative data)
d. The initial rate of penetration in the epidermis
e. The maximum quantity that has penetrated the epidermis
a. Penetration kinetics profile in the epidermis:
FIG. 2

The release kinetics of compound A obtained for the oil in water type emulsion without emulsifier exhibit a high initial gradient followed by a ceiling during which the penetration of compound A no longer increases in the course of time. The reference formula (gel) shows the same kinetics with rapid release for the first few hours, after which a plateau is reached.

As seen in Section 1 ("Single time" cutaneous penetration study), these two formulae have different penetration levels at 16 h, and the penetration of compound A in the epidermis after application of the oil in water emulsion without emulsifier tends to be higher than that obtained after application of the reference gel.

Initial rate of the kinetics:
The initial value of the rate of the kinetics or gradient in the first 3 hours is 4.2 ng/cm$^2$/h.
Maximum quantity in the epidermis:
The maximum quantity in the epidermis is 18.7 ng/cm$^2$.

Example 4

Tolerance Study

In this study:
10 subjects received 2 grams of gel (reference gel) applied to 1000 cm$^2$ for 4 weeks.
A reference gel is understood to mean a gel described as follows:

| Constituents | % |
|---|---|
| Compound A | 0.01 |
| Propylene Glycol | 30.00 |
| Ethanol 95-96% | 67.99 |
| Klucel HF Pharma | 2.00 |

10 subjects received 2 grams of Cream B (oil in water emulsion without emulsifier-Formula 1) applied to 1000 cm$^2$ for 4 weeks.

During the study the investigators had the opportunity of changing the area of application where irritation was excessive.

The results of the study are presented in the table below: The numerical values are the number of patients for whom a change of area was made (value N in the table), and the value in brackets is the percentage corresponding to N.

Development of the percentage of subjects for whom there is no change of area of application

| | | Gel 50 μg/g 1000 cm$^2$ | Cream B 50 μg/g 1000 cm$^2$ | Gel 50 μg/g 2000 cm$^2$ | Gel 100 μg/g 1000 cm$^2$ | Gel 25 μg/g 1000 cm$^2$ |
|---|---|---|---|---|---|---|
| Day 2 | N (%) | — | — | — | — | — |
| Day 4 | N (%) | 1 (10) | — | — | — | — |
| Day 5 | N (%) | — | 1 (10) | 2 (20) | 1 (10) | — |
| Day 6 | N (%) | 1 (10) | — | — | 1 (10) | — |
| Day 7 | N (%) | — | — | 2 (20) | 1 (10) | 1 (10) |
| Day 8 | N (%) | 1 (10) | 1 (10) | — | 2 (20) | 1 (10) |
| Day 9 | N (%) | 3 (30) | 1 (10) | 2 (20) | 1 (10) | — |
| Day 10 | N (%) | — | — | 1 (10) | 1 (10) | 1 (10) |
| Day 11 | N (%) | 2 (20) | 1 (10) | — | 1 (10) | 1 (10) |
| Day 12 | N (%) | — | 1 (10) | 1 (10) | — | 1 (10) |
| Day 13 | N (%) | — | 1 (10) | — | — | — |
| Day 14 | N (%) | 1 (10) | 1 (10) | 2 (20) | 1 (10) | 2 (20) |
| Day 16 | N (%) | 1 (10) | 1 (10) | — | 1 (10) | — |
| Day 18 | N (%) | — | — | — | — | 1 (10) |
| Day 19 | N (%) | — | — | — | — | — |

-continued

| | | Gel 50 μg/g 1000 cm² | Cream B 50 μg/g 1000 cm² | Gel 50 μg/g 2000 cm² | Gel 100 μg/g 1000 cm² | Gel 25 μg/g 1000 cm² |
|---|---|---|---|---|---|---|
| Day 24 | N (%) | — | 1 (10) | — | — | 1 (10) |
| No change in the course of the study | N (%) | — | 1 (10) | — | — | 1 (10) |

FIG. 3

FIG. 3 shows the percentage of subjects for whom there was no change in the area of application as a function of the day of application.

For example, on day 5, for 90% of the subjects receiving Cream B, there was no need to change the area of application. In other words, 10% of the subjects who received Cream B suffered from an irritation requiring a change of area of application.

It is therefore established that the irritation occurs more quickly in the subjects who received the gel than in the subjects who received Cream B. A marked difference is observed from day 9 onwards.

The invention claimed is:

1. A pharmaceutical composition comprising:
an oily phase comprising at least one compound of formula (I)

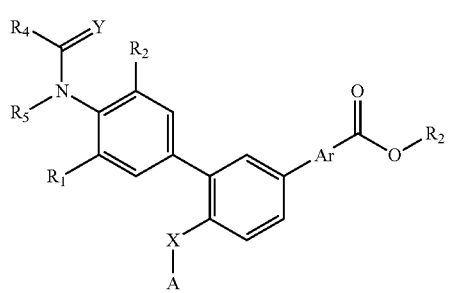

where:
R$_1$ is a hydrogen atom, an alkyl radical of 1 to 4 carbons or a —CF$_3$ radical;
R$_2$ is a hydrogen atom, an alkyl or alkoxy radical of 1 to 4 carbon atoms or a chlorine atom;
R$_3$ is a hydrogen atom, a linear or branched alkyl or alkoxy radical of 1 to 10 carbon atoms optionally substituted by a methoxy group;
R$_4$ is a hydrogen atom or an alkyl radical of 1 to 3 carbon atoms;
R$_5$ is a hydrogen atom or an alkyl radical of 1 to 3 carbon atoms;
or R$_4$ and R$_5$ together form, with the —N—C(=Y)— bond, a ring of the pyrrolidine, pyrrolidinone, piperidine or piperidinone ring;
Y denotes two hydrogen atoms or a heteroatom;
Ar denotes a 1,4-phenyl, 2,5-pyridyl, 5,2-pyridyl or 2,5-thiophenyl ring;
X denotes an oxygen atom, optionally substituted by an alkyl or alkylamine chain or a single C—C bond; and A denotes a hydrogen atom or the following formula:

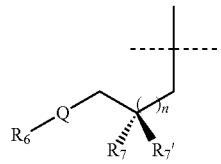

where
Q is an oxygen atom or a —NH— bond;
R$_6$ denotes a hydrogen atom, an alkyl radical of 1 to 6 carbon atoms, a cycloalkyl radical of 3 to 6 carbon atoms, a —C(O)CH$_2$ or —C(O)CH$_2$CH$_3$ radical;
R$_7$ and R$_7$' denote, independently of each other, a hydrogen atom or a hydroxyl group on condition that R$_7$ and R$_7$' are not at the same time a hydroxyl group; and
n is equal to 0, 1, 2, 3, 4 or 5;
at least a principal solvent of compound of formula(I) and at least a co-solvent oil of compound of formula(I);
and an aqueous phase comprising at least a gelifying agent.

2. The composition according to claim 1, wherein the compound of formula (I) is defined so that:
R1 is a hydrogen atom, the t-butyl or i-propyl radical;
R2 is a hydrogen atom, the t-butyl or i-propyl radical;
R3 is a hydrogen atom or the ethyl radical;
R4, R5 are independently from each other the methyl or ethyl radical or together form a pyrrolidine ring; and
A, as previously defined, where R$_6$ denotes a hydrogen atom, the i-propyl or t-butyl radical, a cycloalkyl radical of 3 to 6 carbon atoms, a —C(O)CH$_2$ or —C(O)CH$_2$CH$_3$ radical.

3. The composition according to claim 1, wherein the compound is 3"-tert-butyl-4'-(2-hydroxy-ethoxy)-4"-pyrrolidin-1-yl-[1,1';3',1"]-terphenyl-4-carboxylic acid.

4. The composition according to claim 1, wherein the composition is devoid of a seperate emulsifying agent.

5. The composition according to claim 1, wherein the gelifying agent is selected from the group consisting of:
acrylates/C10-30 alkyl acrylate crosspolymer sold under the name of PEMULEN TR-1 or PEMULEN TR-2,
polyacrylamide gelifiers,
a mixture polyacrylamide/isoparaffin C13-14/laureth-7 sold under the name of SEPIGEL 305,
carbomers sold under the names of ULTREZ 20®, ULTREZ 10®, CARBOPOL 1382® or CARBOPOL ETD2020NF®, CARBOPOL 981 and CARBOPOL 980,
xanthan gum, gellan gum sold under the name of KELCO-GEL, guar gum and cellulose polysaccharides,
aluminium magnesium silicates,
acrylic polymers linked to hydrophobic chains,
modified starches their mixtures, and
carrageenans.

6. The composition according to claim 1, wherein the principal solvent is selected from the group consisting of benzyl alcohol, laureth-4, phenoxyethanol, propylene glycol monocaprylate, pentylene glycol and dimethyl isosorbide.

7. The composition according to claim 1, wherein the principal solvent is phenoxyethanol.

8. The composition according to claim 1, wherein the co-solvent oil is selected from the group consisting of caprylic/capric triglycerides, sweet almond oil, propylene glycol monocaprylate, propylene glycol laurate, sorbitan sesquioleate, diisopropyl adipate, PPG-15 stearyl ether, and apricot kernel oil PEG-6 ester.

9. The composition according to claim 1, wherein the composition also contains one or more additives selected from the group consisting of:
- a preservative system selected from the group consisting of methyl parabene, propyl parabene, benzalkonium chloride, phenoxyethanol sold under the name of PHENOXETOL, benzyl alcohol, potassium sorbate, benzoic acid, 2-bromo-2-nitropropane-1,3-diol sold under the name of BRONOPOL, chlorohexidine, chlorohexidine digluconate, chlorocresole, ethyl alcohol and diazolidinyl urea,
- chelating agents mixtures thereof,
- antioxidants, and
- palliatives and anti-irritants.

10. The composition according to claim 1, wherein the composition can also contain a mineral oil.

11. The composition according to claim 1, wherein the composition can also contain a moistening agent.

12. The composition according to claim 1, wherein the composition can also contain a silicone oil.

13. The composition according to claim 1, wherein the composition can also contain ethanol.

14. The composition according to claim 1, wherein the composition comprises the following ingredients:
- from 0.00001% to 1% w/w of 3"-tert-butyl-4'-(2-hydroxyethoxy)-4"-pyrrolidin-1-yl-[1,1':3',1"]-terphenyl-4-carboxylic acid
- from 0.005 to 10% w/w of gelifying agent for the aqueous phase
- from 0.2 to 5% w/w of solvent
- from 0.5 to 50% w/w of co-solvent oil
- from 0 to 20% w/w of mineral oil
- from 0 to 50% w/w of polyol
- from 0 to 10% w/w of silicone oil
- from 0 to 5% w/w of preservative system
- from 0 to 30% w/w of ethanol
- from 0 to 15% w/w of additives.

15. The composition according to claim 1, wherein the composition is a water in oil emulsion.

16. The composition according to claim 1, wherein the maximum quantity of compound of formula (I) absorbed in the dermis and epidermis 16 hours after application is between 6 ng/cm$^2$ and 19 ng/cm$^2$.

17. The composition according to claim 16, wherein the maximum quantity of compound of formula (I) absorbed in the dermis and epidermis 16 hours after application is between 6.8 ng/cm$^2$ and 10.6 ng/cm$^2$.

18. The composition according to claim 1, wherein the maximum quantity of compound of formula (I) absorbed in the epidermis is attained between 3 hours and 10 hours after application.

19. A medicinal product comprising the composition according to claim 1.

20. A method of treating a pathology, the method comprising administering to a subject afflicted with the pathology an effective amount of the composition of claim 1, wherein the pathology is selected from the group consisting of:
- dermatological conditions associated with a keratinization disorder relating to cellular differentiation and proliferation selected from the group consisting of common acnes. comedonic acnes, polymorphic acnes, rosaceas, nodulocystic acnes, congiobata, senile acnes and secondary acnes;
- keritinization disorders selected from the group consisting of ichtyoses, ichtyosiform conditions, lamellar ichtyosis, Darner's disease, palmoplantar keratodermias, leukoplasias, pityriasis rubra pilaris and leukoplasiform conditions, cutaneous lichen and mucous (oral) lichen;
- dermatological disorders with an inflammatory immuneallergic component, with or without cellular proliferation disorder, selected from the group consisting of cutaneous psoriasis, mucous psoriasis and ungueal psoriasis, psoriasic rheumatic dermatitis, atopical dermatitis and eczema;
- cutaneous disorders due to exposure to UV radiation, photo-induced and chronological ageing of the skin, and to reduce pigmentations and actinic keratoses, and pathologies associated with chronological or actinic ageing, selected from the group consisting of xerosis, pigmentations and wrinkles;
- a condition associated with benign dermal or epidermal proliferations, whether or not of viral origin, selected from the group consisting of common warts, flat warts, molluscurn contagiosum and verruciform epidermodysplasia, and oral and florid papillomatoses;
- dermatological conditions optionally including immune dermatoses selected from the group consisting of erythematous lupus, and bullous immune diseases and sclerodermia;
- stigmata of epidermal and dermal atrophy induced by local and systemic corticosteroids, and any other form of cutaneous atrophy;
- scarring complaints, to treat and repair stretch marks, and to promote scarring;
- a disorder of fungal origin in the cutaneous region, selected from the group consisting of tinea pedis and tinea versicolor; pigmentation disorders selected from the group consisting of hyperpigmentation, melasma, hypopigmentation and vitiligo; and
- cancerous and pre-cancerouscutaneous and mucous conditions selected from the group consisting of actinic keratoses, Bowen's disease, carcinomas in-situ, keratocanthoma and skin cancers selected from the group consisting of basocellular carcinoma (BCC), spinocellular carcinoma (SCC) and T lymphoma.

21. The composition of claim 1, wherein when Y is a heteroatom, the heteroatom is oxygen or sulphur.

22. The composition of claim 5. wherein the gelifying agent is a sodium acrylamide/acryloyidimethyltaurate/isohexadecane/polysoricate 80 sold under the name of SIMULGEL 600 PHA.

23. The composition of claim 5, wherein the xanthan gum is XANTURAL 180®.

24. The composition of claim 5, wherein the cellulose is selected from the group consisting of a mixture of microcrystalline cellulose and sodium carboxymethylcellulose sold under the name AVICEL CL-611, hydroxypropylmethylcellulose, hydroxyethylcellulose and sodium carboxymethylcellulose.

25. The composition of claim 5, wherein the aluminium magnesium silicate is VEEGUM K.

26. The composition of claim 5, wherein the acrylic polymer is PEG-150/decyl alcohol/SMDI copolymer sold under the name ACULYN 44.

27. The composition of claim 5, wherein the modified starch is a modified potato starch sold under the name STRUCTURE SOLANCE.

28. The composition of claim 5, wherein the carrageenan is selected from the group consisting of the four major families: κ, λ, β, and ω.

29. The composition of claim 9, wherein the chelating agent is selected from thr group consisting of EDTA (ethylene diamine tetraacetric acid) and its salts, dihydroglycerine, citric acid, tartaric acid, gluconolactone sold under the name D-(+)-glucono-delta-lactone mixtures thereof.

30. The composition of claim 9, wherein the antioxidant is vitamin E.

31. The composition of claim 30, wherein the vitamin E is DL alpha tocopherol or tocopherol acetate.

32. The composition of claim 9, wherein the antioxidant is vitamin C.

33. The composition of claim 32, wherein the vitamin C is ascorbyl palmitate or butylhydroxy toluene.

34. The composition of claim 9, wherein the palliative or anti-irrant is PPG-12/SMDI copolymer under the name POLYOLPREPOLYMER-2, glycyrrhetinic acid, hyaluronic acid, sodium hyaluronate or an allantoin sold under the name RONACARE ALLANTOINE.

35. The composition of claim 14, wherein the composition comprises from 0.0001% to 0.1% w/w of 3"-tert-butyl-4'-(2-hydroxy-ethoxy)-4"-pyrrolidin-1-yl-[1,1':3',1"]-terphenyl-4-carhoxylic acid.

36. The composition of claim 14, wherein the composition comprises from 0.001% to 0.1% w/w of 3'-tert-butyl-4"-(2-hydroxy -ethoxy)-4"-pyrrolidin-1-yl-[1,1':3',1"]-terphenyl-4-carboxylic acid.

37. The composition of claim 14, wherein the composition comprises from 1% to 5% w/w of gelifying agent for the aqueous phase.

38. The composition of claim 14, wherein the composition comprises from 0.5% to 2% w/w of principal solvent.

39. The composition of claim 14, wherein the composition comprises from 4% to 30% w/w of co-solvent oil.

40. The composition of claim 14, wherein the composition comprises from 0% to 5% w/w of mineral oil.

41. The composition of claim 14, wherein the composition comprises from 5% to 35% w/w of polyol.

42. The composition of claim 14, wherein the composition comprises 0% to 4% w/w of silicone oil.

43. The composition of claim 14, wherein the composition comprises from 0.01% to 2% w/w of preservative system.

44. The composition of claim 14, wherein the composition comprises from 0% to 10% w/w of ethanol.

45. The composition of claim 14, wherein the composition comprises from 0.1% to 10% w/w of additives.

46. The composition according to claim 3, wherein the gelifying agent is selected from the group consisting of:
   acrylates/C10-30 alkyl acrylate crosspolymers sold under the name of PEMULEN TR-1 or PEMULEN TR-2,
   polyacrylamide gelifiers,
   a mixture polyacrylamide/isoparaffin C13-14/laureth-7 sold under the name of SEPIGEL 305,
   carbomers sold under the names of ULTREZ 20®, ULTREZ 10®, CARBOPOL 1382® or CARBOPOL ETD2020NF®, CARBOPOL 981 and CARBOPOL 980,
   xanthan gum, gellan gum sold under the name of KELCO-GEL, guar gum and cellulose polysaccharides,
   aluminum magnesium silicates,
   acrylic polymers linked to hydrophobic chains,
   modified starches and their mixtures, and
   carrageenans.

47. The composition according to claim 3, wherein the principal solvent is selected from the group consisting of benzyl alcohol, laureth-4, phenoxyethanol, propylene glycol monocaprylate, pentylene glycol and dimethyl isosorbide.

48. The composition according to claim 3, wherein the principal solvent is phenoxyethanol.

49. The composition according to claim 3, wherein the co-solvent oil is selected from the group consisting of caprylicicapric triglycerides, sweet almond oil, propylene glycol monocaprylate, propylene glycol laurate, sorbitan sesquioleate, diisopropyl adipate, PPG-15 stearyl ether, and apricot kernel oil PEG-6 ester.

50. The composition according to claim 3, wherein the composition also contains one or more additives selected from the group consisting of:
   a preservative system selected from the group consisting of methyl parabene, propyl parabene, benzalkoniurn chloride, phenoxyethanol sold under the name of PHENOX-ETOL, benzyl alcohol, potassium sorbate, benzoic acid, 2-bromo-2-nitropropane-1,3-diol sold under the name of BRONOPOL, chlorhexidine, chlorhexidine digluconate, chlorocresole, ethyl alcohol and diazolidinyl urea,
   chelating agents and mixtures thereof,
   antioxidants, and
   palliatives and anti-irritants.

51. The composition according to claim 3, wherein the composition can contain a mineral oil.

52. The composition according to claim 3, wherein the composition can also contain a moistening agent.

53. The composition according to claim 3, wherein the composition can also contain a silicone oil.

54. The composition according to claim 3, wherein the composition can also contain ethanol.

55. The composition according to claim 3, wherein the composition is a water in oil emulsion.

56. The composition according to claim 3, wherein the maximum quantity of said compound absorbed in the dermis and epidermis 16 hours after application is between 6.8 ng/cm$^2$ and 19 ng/cm$^2$.

57. The composition according to claim 3, wherein the maximum quantity of said compound absorbed in the dermis and epidermis 16 hours after application is between 6.8 ng/cm$^2$ and 10.6 ng/cm$^2$.

58. The composition according to claim 3, wherein the maximum quantity of said compound absorbed in the epidermis is attained between 3 hours and 10 hours after application.

59. A medicinal product comprising the composition according to claim 3.

60. A method of treating a pathology, the method comprising treating a subject afflicted with the pathology with an effective amount of the composition according to claim 3, wherein the pathology is selected from the group consisting of:
   dermatological conditions associated with a keratinization disorder relating to cellular differentiation and proliferation selected from the group consisting of common ernes, comedonic acnes, polymorphic acnes, rosaceas, nodulocystic acnes, conglobata, senile acnes and secondary acnes;
   keritinization disorders selected from the group consisting of ichtyoses, ichtyosiform conditions, lamellar ichtyosis, Darner's disease, palmoplantar keratodermias, leukoplasias, pityriasis rubra pilaris and leukoplasiform conditions, cutaneous lichen and mucous (oral) lichen;
   dermatological disorders with an inflammatory immune-allergic component, with or without cellular proliferation disorder, selected from the group consisting of cutaneous psoriasis, mucous psoriasis and ungueal psoriasis, psoriasic rheumatic dermatitis, atopical dermatitis and eczema;

cutaneous disorders due to exposure to UV radiation, photo-induced and chronological ageing of the skin, and to reduce pigmentations and actinic keratoses, and pathologies associated with chronological or actinic ageing, selected from the group consisting of xerosis, pigmentations and wrinkles;

a condition associated with benign dermal or epidermal proliferations, whether or not of viral origin, selected from the group consisting of common warts, flat warts, molluscum contagiosum and verruciform epidermodysplasia, and oral and florid papillomatoses;

dermatological conditions optionally including immune dermatoses selected from the group consisting of erythematous lupus, and bullous immune diseases and sclerodermia;

stigmata of epidermal and dermal atrophy induced by local and systemic corticosteroids, and any other form of cutaneous atrophy;

scarring complaints, to treat and repair stretch marks, and to promote scarring;

a disorder of fungal origin in the cutaneous region, selected from the group consisting of tinea pedis and tinea versicolor;

pigmentation disorders selected from the group consisting of hyperpigmentation, melasma, hypopigmentation and vitiligo; and cancerous and pre-cancerous cutaneous and mucous conditions selected from the group consisting of actinic keratoses, Bowen's disease, carcinomas in-situ, keratocanthoma and skin cancers selected from the group consisting of basocellular carcinoma (BCC), spinocellular carcinoma (SCC) and T lymphoma.

61. The composition according to claim 46, wherein the gelifying agent is a sodium acrylamidetacryloyldimethyltaurate/isohexadecaneipolysorbate 80 sold under the name of SIMULGEL 600 PHA.

62. The composition according to claim 46, wherein the xanthan gum us XANTURAL 180®.

63. The composition according to claim 46, wherein the cellulose is selected from the group consisting of a mixture of microcrystalline cellulose and sodium carboxymethylcellulose sold under the name AVICEL CL-611, hydroxypropylmethylcellulose, hydroxyethylcellulose and sodium carboxymethylcellulose.

64. The composition according to claim 46, wherein the aluminum magnesium silicate is VEEGUM K.

65. The composition according to claim 46, wherein the acrylic polymer is PEG-150/decyl alcohol/SMDI copolymer sold under the name ACULYN 44.

66. The composition according to claim 46, wherein the modified starch is a modified potato starch sold under the name STRUCTURE SOLANCE.

67. The composition according to claim 46, wherein the carrageenan is selected from the group consisting of the four major families: κ, λ, β, and ω.

68. The composition according to claim 50, wherein the chelating agent is selected from the group consisting of EDTA (ethylene diamine tetraacetric acid) and its salts, dihydroglycerine, citric add, tartaric add, gluconolactone sold under the name D-(+)-glucono-delta-lactone and mixtures thereof.

69. The composition according to claim 50, wherein the antioxidant is vitamin E.

70. The composition according to claim 69, wherein the vitamin E is DL alpha tocopherol or tocopherol acitate.

71. The composition according to claim 50, wherein the antioxidant is vitamin C.

72. The composition according to claim 71, wherein the vitamin Cis ascorbyl palmitate or butylhydroxytoluene.

73. The composition according to claim 50, wherein the palliative or anti-irritant is PPG-12/SMDI copolymer under the name POLYOLPREPOLYMER-2, glycyrrhetinic add, hyaluronic add, sodium hyaluronate or an allantoin sold under the name of RONACARE ALLANTOINE.

* * * * *